United States Patent [19]

Johnson

[11] Patent Number: 5,492,547
[45] Date of Patent: Feb. 20, 1996

[54] PROCESS FOR PREDICTING THE PHENOTYPIC TRAIT OF YIELD IN MAIZE

[75] Inventor: Richard Johnson, Urbana, Ill.

[73] Assignee: DeKalb Genetics Corp., DeKalb, Ill.

[21] Appl. No.: 121,391

[22] Filed: Sep. 14, 1993

[51] Int. Cl.$^6$ ............................... A01H 1/00; C12N 15/00
[52] U.S. Cl. .................... 47/58; 435/172.3; 800/DIG. 56
[58] Field of Search ............................. 435/172.3, 172.1, 435/6; 935/76; 47/58.05, 58.03

[56] References Cited

U.S. PATENT DOCUMENTS

| | | | |
|---|---|---|---|
| 4,626,610 | 12/1986 | Sun | 800/1 |
| 4,670,388 | 6/1987 | Rubin et al. | 435/172.3 |

FOREIGN PATENT DOCUMENTS

| | | | |
|---|---|---|---|
| 0306139 | 1/1988 | European Pat. Off. | 435/172.3 |
| 0317239 | 12/1988 | European Pat. Off. | 435/172.3 |
| 84/04758 | 3/1984 | WIPO | 435/172.3 |
| 89/07647 | 6/1989 | WIPO | 435/172.3 |
| 90/04651 | 5/1990 | WIPO | 435/172.3 |

OTHER PUBLICATIONS

Lande & Thompson, "Efficiency of Marker-Assisted Selection in the Improvement of Quantitative Traits," Genetics, 124:743–756, 1990.
Keim et al., "RFLP Mapping in Soybean: Association Between Marker Loci and Variation in Quantitative Traits," Genetics, 126:735–742, 1990.
Michelmore & Shaw, "Character Dissection," Nature, News and Views, 335:672–673, 1988.
Paterson et al., "Resolution of quantitative traits into Mendelian factors by using a complete linkage map of restriction fragment length polymorphisms," Nature, 335:721–726, 1988.
Nienhuis et al., "Restriction Fragment Length Polymorphism Analysis of Loci Associated with Insect Resistance in Tomato," Crop Sci., 27:797–803, 1987.
Lander & Botstein, "Mapping Mendelian Factors Underlying Quantitative Traits Using RFLP Linkage Maps," Genetics, 121:185–199, 1989.
Tanksley et al., Bio/Technology, 7:257–264, 1989.
Asins & Carbonell, Theor. Appl. Genet., 76:623–626, 1988.
Weller et al., Biol. Abstr., 85(9), Abstract #90101, 1988.
Helentjaris, Trends in Genetics, 3(8):217–221, 1987.
Osborn et al., Theor. Appl. Genet., 73:350–356, 1987.
Helentjaris & Shattuck-Eidens, Maize Genetics Corp. Newsletter, pp. 88–89, 1987.
Weller, Biol. Abstr., 85(6), Abstract #57768, 1988.
Weller, Biol. Abst., 83, Abstract #3756, 1987.
Lander et al., Genomics, 1(2):174–181, 1987.
Helentjaris, J. Cell. Biochem. Suppl. 11(3):56, Abstract #F429, 1987.
Helentjaris, Am. J. Botany, 74(5):665, Abstract #197, 1987.
Beckman & Soller, Oxford Surveys of Plant Molecular and Cellular Biology, 3:196–250, 1986.
Helentjaris et al., Theor. Appl. Genet., 72:761–769, 1986.
Evola et al., Theor. Appl. Genet., 71:765–771, 1986.
Bernatzky & Tanksley, Genetics, 112:887–898, 1986.
Smith & Simpson, Biol. Abstr. 82(12), Abstract #108250.
Soller & Beckman, Biol. Abstr. 82, Abstract #86937.
Helentjaris et al., Plant Mol. Biol., 5:109–118, 1985.

(List continued on next page.)

Primary Examiner—Gary Benzion
Attorney, Agent, or Firm—Arnold, White & Durkee

[57] ABSTRACT

This invention relates to a method for improving the efficacy of a plant breeding program which has as its goal to selectively alter phenotypic traits that are capable of being described numerically and are under the control of quantitative trait loci (QTLs). The method combines the newer techniques of molecular biology with modifications of classical pedigree breeding strategies. Progeny performance is predicted on the basis of at least one secondary trait, facilitating selection strategies. In particular, regression estimates are obtained by determining the relationship between selected inherited marker loci and quantitative phenotypic trait values in predictor populations, and used in combination with inherited marker profiles of plants, to implement a selection strategy in related populations.

7 Claims, 21 Drawing Sheets

OTHER PUBLICATIONS

Soller & Beckman, Theor. Appl. Genet., 67:25–33, 1983.
Tanksley et al.., Biol. Abstr. 76(6):4509, Abstract #41484.
Tanksley et al., Biol. Abstr. 73(10):7132, Abstract #68480.
Cox, "The FLP protein of the yeast 2–μm plasmid: Expression of a eukaryotic genetic recombination system in *Escherichia coli*", *Proc. Natl. Acad. Sci. USA, 80:4223–4227, 1983.*
Edwards, et al., "Molecular–Marker–Facilitated Investigations of Quantitative–Trait Loci in Maize. I. Numbers, Genomic Distribution and Types of Gene Action", *Genetics*, 116:113–125, 1987.

Jensen, "Selection Indices", *In Plant Breeding Methodology, Wiley Interscience,* 25:355–378, 1981.

Larson and Hanway, "Corn Production", Chapter 11, 625–669.

Ou–Lee et al., "Expression of a foreign gene linked to either a plant–virus or a *Drosophila* promoter, after electroporation of protoplasts of rice, wheat and sorghum", *Proc. Natl. Acad. Sci. USA,* 83:6815–6819, 1986.

Poehlman, "Progeny Test Versus Combining Ability Test", *Breeding Field Crops,* Third Edition, p. 216.

Stuber et al. (1987) Crop Science vol. 27:639–648.

PROCESS FOR PREDICTING THE PHENOTYPIC TRAIT OF YIELD IN MAIZE

DESCRIPTION

TECHNICAL FIELD OF THE INVENTION

This invention relates to a process of predicting the value of a phenotypic numerically representable trait in a plant. A process of the present invention uses a quantitative assessment of the distribution of the numerically representable trait and a genotypic database in a first population to define an association between genotype and phenotype and predict the value of the phenotype in the same or a different plant.

BACKGROUND OF THE INVENTION

Phenotypic traits of agronomic interest tend to be quantitative and continuously distributed. For most such traits, the quantitative distributions, resulting when values of individual plants are graphed against their relative frequency, fit that expected from segregation of alleles at a large number of loci, with each locus (a position on a chromosome) contributing a relatively small amount to the value of the phenotype. This is the polygenic model of inheritance. Another assumption of the basic model is that heritable gene action is additive; that is, each allele contributes some predictably inheritable amount to the total quantitative value of the phenotype. Environmental and unpredictable heritable factors are then superimposed as variation on the genotypic sources of variation to yield the phenotypic variance component of the continuous distribution of the trait. Distributions may be described by moments, notably the mean and variance (or the standard deviation which is the square root of the variance).

Before the polygenic model was developed, the observation of continuous distributions of traits initially posed an obstacle to the universal application of Mendelian theory. This apparent conflict was resolved by proposing the polygenic model for the inheritance of traits that could be described quantitatively (e.g., corn ear length, number of kernels, plant height, yield in bushels). The model proposed an underlying segregation of single genetic entities, thereby being consistent with Mendelian theory. However, because the effects of these individual genes were aggregated in the expression of the quantitative phenotypes, their individual effects could not be teased out. (Johannsen, 1909; Nilsson-Ehle, 1909; East, 1916; Fisher, 1918). Environmental variation further smoothed the distribution, masking boundaries between distinct genotypic classes.

The polygenic model has been used in attempts to enhance selection efficacy in plant breeding programs. By observation and careful measurements of results of various parental-offspring distributions, both in plants and animals, and by expressing the genetic relationships in mathematical correlations, a complex mathematical theory emerged (Fisher; 1918; Falconer, 1960; Wright, 1968, 1977).

A basic tenant of this theory is the expression of phenotypic distribution in terms of its variance and to dissect that variance into its causative components. By studying the variance in offspring distributions where the offspring result from various types of crosses, and by determining the correlation between phenotypic distributions of different pedigree relationships (parent-offspring, offspring of the same cross, subsequent generations, e.g., $F_2$–$F_3$) it was determined that the phenotypic variance ($V_P$) had as basic components genotypic variance ($V_G$) and environmental variance ($V_E$). In a simple case, the variance of plants of the same genotype grown in different environments provides an estimate of the effects of environment. Factors contributing to the environmental variance include year of growth and differences in the soil composition of plots of land.

In turn, each of these components could be further subdivided, for example, by separating $V_G$ into additive ($V_A$), dominance ($V_D$) and epistatic ($V_I$) components. The components of the variance could be estimated by breeding experiments. These values were then used to predict results of other breeding crosses. Response to selection was found to be a function of the heritability of the trait, the selection differential and the intensity of selection.

The heritability ($h^2$) of a trait is broadly defined as $$h^2 = \frac{V_G}{V_P},$$

or more narrowly, $$h^2 = \frac{V_A}{V_P}$$

and is a predictor of the degree to which values of traits may be transmitted from parents to offspring.

The intensity of selection is defined as the percent of the distribution from which the parents of the next generation are derived. The selection differential is defined as the difference between the trait in the parental population versus that of the selected parents. The cost effectiveness of selection is determined by the amount of time (in generations) required to achieve a significant change in the distribution of the trait under selection, the number of parents selected for breeding, and the response to selection. The response to selection is the difference between parental and offspring means after selection, e.g., after a generation of selective breeding. The basic mathematical formula to predict gain from selection is as follows:

expected gain=(selection differential)×(heritability)

where selection differential is the mean value of the phenotypic trait in the selected individuals minus the overall parental population mean, and heritability is the proportion of the phenotypic variance that is due to additive genetic variance.

A change of the population mean brought about by selection, i.e., the response to selection, depended on the heritability of a trait and on the intensity of selection (selection differential). This variable depends on the proportion of the population selected, and the standard deviation of the phenotypic trait. The shaded area of the distributions of FIG. 2A, FIG. 2B and FIG. 2C are the proportion selected, and S is the selection differential.

Despite concerted attempts to improve commercially important phenotypic traits in plants, the rate of improvement of those traits has been only a few to several percent of the mean per year for the past several decades. In many previously described breeding programs, plants are selected as parents of the next generation on the basis of one or more phenotypic traits (e.g., yield in bushels per acre, number of rows per kernel of corn, percentage of grain oil).

A problem associated with selection based on phenotype is the affect of the environment on that phenotype. For various crop plants, it has been established that roughly half of improvement is due to improved husbandry practices, i.e., environmental effects rather than genetic changes effected by selection. (Lande and Thompson, 1990). For example, over the past 60 years, increases in yield due to genetic improvement have averaged only about one bushel/acre/year (Hallauer, et al., 1988, p. 466). Only a small population of hybrid plants produced commercially ever show enough improvement to be worth marketing. Environmental variables which need to be taken into account include soil type and the amount and distribution of rainfall. One of the important and influential environmental conditions is the temperature range of the climate in which the plants are grown. The time period needed by the plants to reach maturity (growth period) is under genotypic control. For optimum growth, the genotypically based growth period of the plant must fit within the environmental range. For example, if the plant does not fulfill its reproductive potential before the temperature drops below a threshold, the plant will not produce seed or offspring in that environment. Comparison of plants for various traits is typically made among plants of similar or identical maturity.

Another problem of phenotype selection is polygenic control. Most phenotypic traits of commercial interest are under polygenic, rather than single locus, control. This means that expression of alleles at many loci contribute to the phenotype of interest. Polygenically controlled traits, therefore, are not solely determined by any particular locus. Consequently, selecting on the basis of phenotype is a superficial and inefficient strategy. Complex genetic phenomenon lurk underneath the phenotypic facade. A tortuous, rather than a direct path, links the phenotype and genotype. At best, previous methods for predicting progeny performance were based only on filial relationships, displayed diminished effectiveness when applied to contiguous generations, and were available only on a population basis, not for individual plants.

The basic concept of selection described above has been applied in specific breeding schemes. Success has been a function of how well inheritance of a trait fits the assumptions of the polygenic model, and of the factors discussed above. An important application of these polygenic models was in selective breeding programs aimed at channeling the values of the phenotype toward one end or the other of its distribution. Selection entails choosing a sample of potential parents, the sample being based on the value of the plants for the traits being selected.

An example of a plant for which selective breeding has been practiced is corn (Sprague and Eberhart, 1977). Until this century, only crude mass selection was practiced; each ear of corn was harvested separately, and the most desirable ears were used to plant the ensuing crop. Information on the effectiveness of this method was almost completely lacking, although variation among races and varieties of corn existing at the turn of the century suggested some effect (Sprague and Eberhart). One of the most commercially important traits, "yield," was found to be the least amenable to change. Unexpectedly, this is a trait for which a process of the present invention has proved to be efficacious.

The next progression in selective breeding was "ear-to-row selection" in which the progeny of selected ears were separately evaluated by field planting and assessing the phenotypic distribution of the resulting plants. If a trait of interest was controlled by a few genes, genetic effects were not masked by environmental variation and a large number of plants could be grown for evaluation of phenotypic traits. Selective breeding to concentrate desirable genes in a population subsample, would be relatively straightforward. In reality, there were many problems attending selection of most traits of commercial interest. Exemplary such problems were: 1) control by a large number of genes (polygenic); 2) genetic effects were masked by the environment; 3) a complicated system of genetic interactions existed; and 4) the methods of isolating and evaluating lines were not wholly adequate.

Many recurrent selection methods and techniques have been proposed to improve breeding populations. Their general theme is to repeatedly select plants based on their apparently superior phenotypes and to interbreed these to form a new improved population. The assumption is that the frequency of alleles underlying the superior phenotypes will increase in frequency due to selection. Because a large number of loci are believed to control important commercially desirable phenotypic traits (e.g., yield), classical selection leads to very slow changes in the mean and genetic variance of this trait. Gene frequencies change gradually because each locus has only a small aggregate affect on the phenotypic trait as a whole.

Gain from selection can theoretically be enhanced by increasing the selection intensity (which means selecting a small elite percentage of the population as parents). However, there are risks in this approach. Key genetic factors may be excluded if the sample is too small, or deleterious effects of inbreeding may appear.

The trials and tribulations of breeders who used some of the selection methods to improve yield in corn are presented by Sprague and Eberhart (1977). Superiority (heterosis) of hybrid plants resulting from some crosses was noted even before the modern genetic theory provided insights regarding this phenomenon. Heterosis likely resulted from partial to complete dominance, overdominance, epistasis, or some combination of these phenomena. If partial to complete dominance predominates, a possibility exists or eventual development of stable, high-yielding homozygous genotypes. If overdominance or certain types of epistasis predominate, however, the highest yielding genotypes must be heterozygotes.

SUMMARY OF THE INVENTION

In one aspect, the present invention provides a process for predicting the value of a numerically representable phenotypic trait in a plant of a given species. That process comprises the steps of:

(a) forming a phenotypic trait database in a first plant population of the species by quantitatively assessing the distribution of a numerically representable phenotypic trait in the first plant population;

(b) forming a first genotypic database in the first plant population by genotyping members of the first plant population tier one or more inherited genetic markers;

(c) evaluating the phenotypic trait database in conjunction with the first genotypic database to define an association between the numerically representable phenotypic trait and the inherited genetic marker(s);

(d) forming a second genotypic database in a second plant population of the species by genotyping members of the second plant population for the inherited genetic marker; and (e) predicting the values of the numerically representable phenotypic trait of all members of the second plant population using the association and the second genotypic database.

In a preferred embodiment, the association is a regression equation where the numerically representable phenotypic trait is a dependent variable and the inherited genetic markers are independent variables. In another embodiment, the first and the second plant populations are both derived from the same seminal $F_1$ hybrid, the second plant population being at the same or an advanced generation as the first plant.

Preferably, quantitatively assessing comprises testcrossing to obtain progeny and quantitatively assessing the distribution in combining ability of the first plant population or making direct observations on progeny derived by artificial or natural self-pollination of the first plant.

A preferred numerically representable phenotypic trait is yield, stalk strength, root strength, disease resistance, insect resistance, grain oil content, grain protein content, grain starch content, or grain moisture content and a preferred plant species is *Zea mays* or *Glycine max*. The inherited genetic marker is preferably inherited in codominant fashion.

In another aspect, the present invention provides a process for predicting the value of a numerically representable phenotypic trait in a plant of a given species, which process comprises the steps of:

(a) initiating a population of plant lines from a seminal $F_1$ hybrid;

(b) evaluating a first population of plant lines at a generation subsequent to that of the seminal $F_1$ hybrid to quantitatively assess the distribution of the numerically representable phenotypic trait of the first plant population;

(c) genotyping members of the first plant population for one or more inherited genetic markers;

(d) estimating the regression in the first plant population of the numerically representable phenotypic trait on at least one of the inherited genetic markers to develop a regression equation;

(e) genotyping members of a second plant population of the species, the second plant population being derived from the same or a different $F_1$ seminal hybrid, the second plant population at the same or an advanced generation relative to the first plant; and (f) predicting in the second plant population the values of the numerically representable phenotypic trait of all members using the regression equation.

In particular embodiments, evaluating comprises testcrossing to obtain progeny and thereby evaluating the distribution of combining ability of the first plant population or making direct observations on progeny of members of the first plant population derived by artificial or natural self-pollination; the plant line is initiated from the seminal $F_1$ hybrid by self-fertilization; the regression equation defines the numerically representable phenotypic trait as a dependent variable and the inherited genetic marker as an independent variable; the numerically representable phenotypic trait is yield, stalk strength, root strength, disease resistance, insect resistance, grain oil content, grain protein content, grain starch, or grain moisture content; the inherited genetic marker is inherited in codominant fashion; the species is *Zea mays* or *Glycine max*; and the first and the second plant are both derived from the same seminal $F_1$ hybrid, the second plant being at the same or an advanced generation as the first plant.

In still yet another aspect, the present invention provides a process of predicting the value of a numerically representable phenotypic trait in a plant of a given species, comprising the steps of:

(a) providing a progenitor plant population by self-pollinating hybrid plants;

(b) testcrossing members of a first plant progenitor population to determine the distribution of combining ability in the first population as expressed values of the numerically representable phenotypic trait in members of the first plant population;

(c) genotyping members of the first plant population to determine a distribution of first genetic marker fingerprints;

(d) expressing an association by a regression equation between the distributions of the numerically representable phenotypic trait and the first genetic marker fingerprint converted to a numerical score;

(e) genotyping a member of a second population of the same or a different progenitor population, the second plant being at a generation at or advanced beyond the generation of the first population to determine a second genetic marker fingerprint;

(f) using the regression equation and the second genetic marker fingerprint converted to a numerical score to predict the value of the numerically representable phenotypic trait in the second plant.

In a still further aspect, the present invention provides a process for predicting the value of a numerically representable phenotypic trait in a plant of a given species, which process comprises the steps of:

(a) determining an association between at least one genetic marker and at least one numerically representable phenotypic trait in a first plant population at a first descendant generation of a first seminal $F_1$ hybrid plant;

(b) genotyping a second plant from a second descendant generation of the same or a different $F_1$ hybrid plant, the second generation at or beyond the first generation;

(c) predicting in the second plant the value of the numerically representable trait by applying an equation that defines an association between at least one of the genetic markers and the numerically representable phenotypic trait in the first plant population.

The present invention further provides a process of predicting the value of a phenotypic trait in a plant of a given species, comprising:

(a) identifying in a first plant population of the species one or more genetic markers that are linked to quantitative trait loci that affect the phenotypic trait;

(b) conducting single locus or interval mapping analysis to estimate in the first plant population additive effects ascribable to each locus or interval based on numerical values of the phenotypic trait;

(c) summing the additive effects;

(d) combining the summed additive effects with testcross or directly observed values to produce an index of genotypic merit;

(e) quantifying the genetic markers in members of a second plant population of the species, the second plant population at an advanced generation relative to the first plant population;

(f) predicting in members of the second plant population the values of the phenotypic trait using the index.

In another aspect, the present invention provides a process of breeding plants comprising:

(a) determining the distribution of allelic variation in a first population of parent lines of a first hybrid plant population;

(b) determining an association in the first hybrid plant population between the genetic markers of the first population of parent lines and one of the phenotypic traits expressed by members of the first hybrid population;

(c) genotyping members of a second population of parent lines for the genetic markers;

(d) selecting members of the second population of parent lines for breeding based on a predicted value of performance for one of the phenotypic traits using a regression equation with the genotypes of members of the second population of parent lines as prediction variables.

BRIEF DESCRIPTION OF THE DRAWINGS

In the drawings which form a portion of the specification:

FIG. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N, FIG. 4O and FIG. 4P are an RFLP linkage map for maize.

DETAILED DESCRIPTION OF THE INVENTION

I. Definitions

Figure 1:
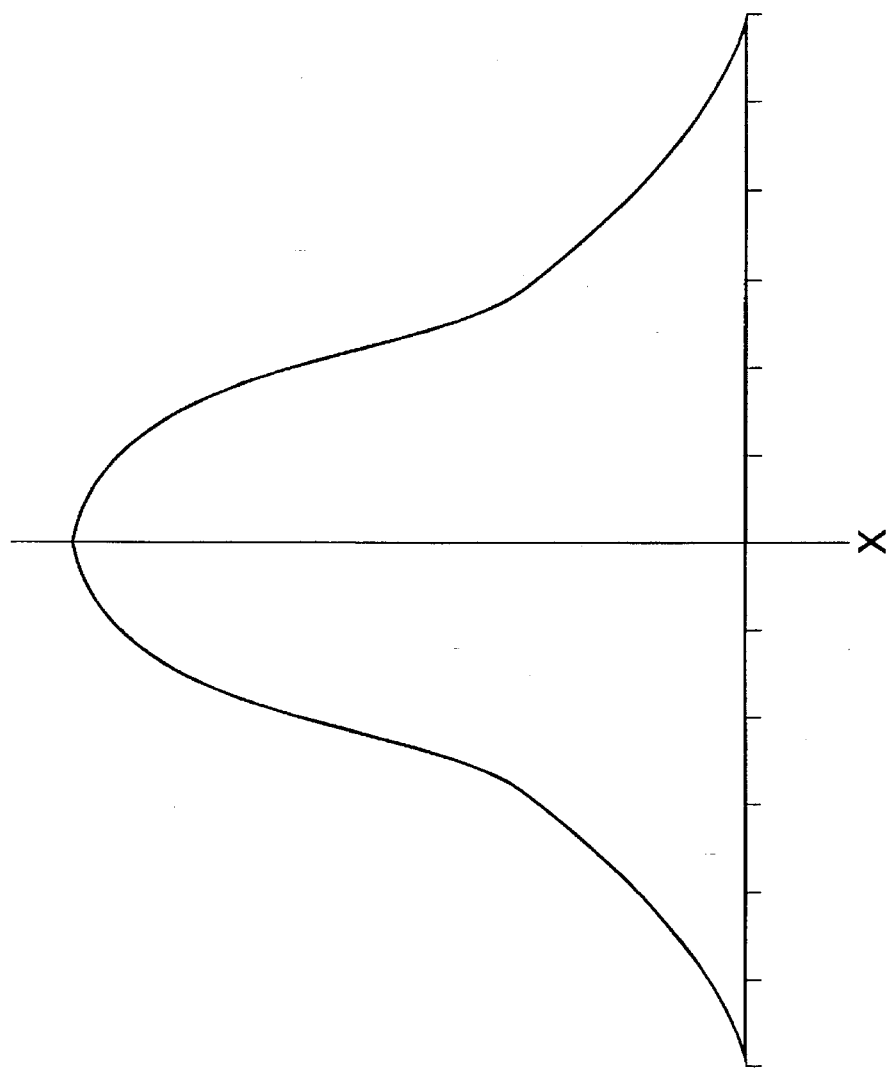
FIG. 1 is a continuous distribution of a numerically representable trait (X) under polygenic control.
Figure 2C:
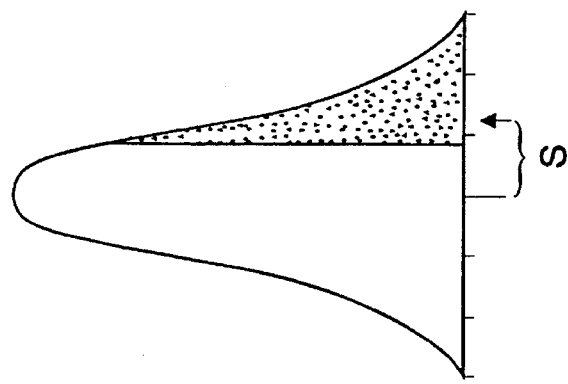
FIG. 2A, FIG. 2B and FIG. 2C illustrate response to selection and the selection differential; (a) 50% selected; standard deviation 2 units; s=1.6 units; (b) 20% selected; s=2.8 units; (c) 20% selected; standard deviation 1 unit; s=1.4 units.
Figure 2B:
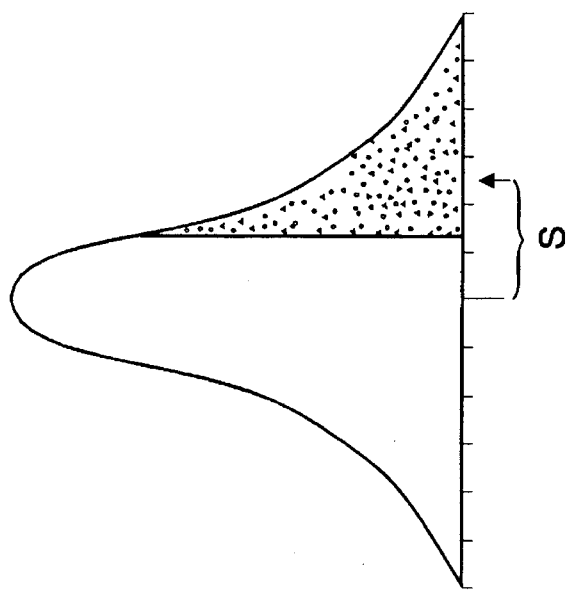
Figure 2A:
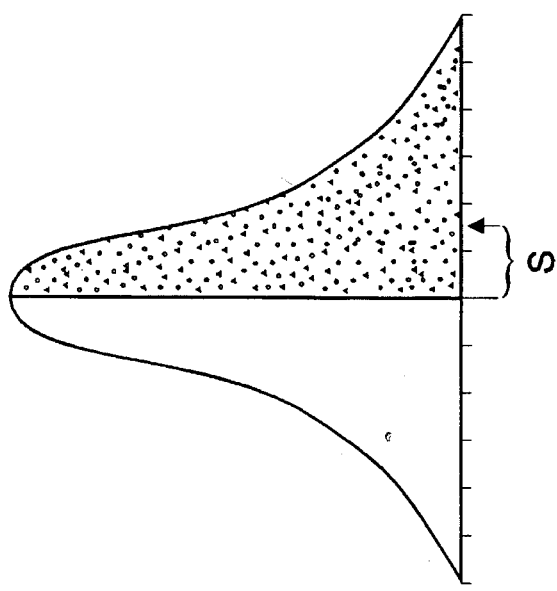

Allele is any of one or more alternative forms of a gene, all of which alleles relate to one trait or characteristic. In a diploid cell or organism, the two alleles of a given gene occupy corresponding loci on a pair of homologous chromosomes.

Backcrossing is a process in which a breeder crosses a first generation hybrid ($F_1$) with one of the parental genotypes one or more times.

Chromatography is a technique wherein a mixture of dissolved substances are bound to a solid support followed by passing a column of fluid across the solid support and varying the composition of the fluid. The components of the mixture are separated by selective elution.

Diploid refers to a cell or organism having two sets of chromosomes.

Electrophoresis is a process by which particles suspended in a fluid are moved under the action of an electrical field, and thereby separated according to their charge and molecular weight. This method of separation is well known to those skilled in the art and is typically applied to separating various forms of enzymes and of DNA fragments produced by restriction endonucleases.

Enzymes are organic catalysts that may exist in various forms called isozymes. Although these isozymes are functionally related, they are structurally (chemically) different. The differences are under single gene, codominant control. Consequently, electrophoretic separation to produce band patterns may be equated to different alleles at the DNA level. Structural differences that do not alter charge cannot be detected by this method.

Filial Relationship is that relationship among generations based solely on their ancestral links as evidenced in pedigrees.

Genotype refers to the genetic constitution of a cell or organism.

Haploid refers to a cell or organism having one set of the two sets of chromosomes in a diploid.

Linkage refers to a phenomenon wherein alleles on the same chromosome tend to segregate together more often than expected by chance if their transmission was independent.

Linkage Disequilibrium refers to a phenomenon wherein alleles tend to remain together in linkage groups when segregating from parents to offspring, with a greater frequency than expected from their individual frequencies.

Marker is a readily detectable phenotype either dominant or codominant, preferably inherited in codominant fashion (both alleles at a locus in a diploid heterozygote are readily detectable), with no environmental variance component, i.e., heritability of 1.

Phenotype refers to the detectable characteristics of a cell or organism, which characteristics are the manifestation of gene expression.

Quantitative Trait Loci (QTL) refer to genetic loci that control to some degree numerically representable traits that are usually continuously distributed.

Testcross is a cross between a plant line with known characteristics, and one of unknown characteristics. The known plant is a standard line, usually of established performance. This type of cross breeding has as its goal, determination of hybrid performance.

Tester is a line or individual plant with a standard genotype, known characteristics and established performance.

II. The Invention

The present invention extends traditional breeding programs and employs novel methods of molecular genetics to maximize improvement in crop characteristics by improving the efficacy of a plant selective breeding program. Preferred plants are corn plants, soybean, sorghum, or any other plant for which commercially desirable traits are to be improved by selective breeding and for which reproduction is achievable by self and/or cross-pollination.

An advantage of a process disclosed herein is the increased ability to predict the value of at least one numerically representable phenotypic trait in a plant line. Such a phenotypic trait is preferably a trait of commercial interest, such as yield, stalk and root strength, oil percentage of grain, or disease and drought resistance.

The present invention extends the selective power from that based on a simple filial relationship to a functional relationship based on actual identification of single locus genetic or inherited markers linked to controlling genes. Such marker-based selection relies on (a) a state of positive linkage disequilibrium; (b) the strength of linkage between a genetic marker and a quantitative trait loci (QTL); and (c) the magnitude of the selected QTL effect. The relationship is more precise than that based on ancestry.

By way of example, if plants designated $F_2$ show a continuous distribution for kernel rows per ear, and parent $F_2$ plants for the $F_3$ generation are selected as those having a specific minimum value for kernel rows per ear, that is, a threshold value cuts off an area of the $F_2$ distribution to be parents, the mean value of kernel rows in the $F_3$ generation can be estimated if heritability is known, but individual $F_3$ plant genetic values cannot be determined without physical evidence regarding the genes themselves. A process of the present invention makes use of the direct paths of single locus inherited genetic markers to select the more elusive polygenic groupings of alleles controlling traits of commercial interest by using the genetic markers as selective indicators.

Such a process incorporates a genetic marker profile with associations calculated in other genotypically related plants between those genetic markers and numerical values of a quantitative phenotypic trait of interest to improve the efficacy of selective breeding programs. In general, such a process is a form of secondary, or indirect selection. Differing from previous methods, however, a process of this invention teaches how to predict progeny performance based on genetic marker-linked performance for quantitative phenotypic traits in other generations and in plants of differing lineage.

A process of the present invention provides for predicting the value of at least one numerically representable phenotypic trait in a plant on the basis of marker-quantitative trait associations ascertained on other plant lines of the same species. Those other plant lines may, but not necessarily include, a progenitor line to the plant for which a prediction is being made. Such a process has unexpectedly produced more precise and accurate predictions of performance then that based directly on the phenotypic value of the progenitors. The most efficacious method of prediction is based on marker-QTL linkages for the phenotypic trait of interest. By way of example, selection on the markers associated with QTL produced greater gain in advanced generation testcross yield then that achievable by selection on early generation testcross yield itself. Thus, markers proved to be not merely aids to phenotypic selection but altogether superior instruments for the selection of the best genotypes (See Examples 1–3 hereinafter).

A. A Process of Predicting Phenotypic Trait Value

In one aspect, the present invention contemplates a process for predicting the value of a numerically representable phenotypic trait in a plant of a given species. In accordance with such a process, a phenotypic and genotypic database are formed in a first plant population. A phenotypic trait database is formed by quantitatively assessing the distribution of a numerically representable phenotypic trait in the first plant population. A genotypic database is formed by genotyping members of a first plant population for at least one inherited genetic marker.

The phenotypic trait database is evaluated in conjunction with the genotypic database to determine an association between a numerically representable phenotypic trait and at least one inherited genetic marker. That association, which expresses the phenotypic trait as a function of the inherited marker is then used to predict the value of the numerically representable phenotypic trait in members of a second plant population of the same species based on the genotyped inherited marker(s) in members of that plant population.

The invention combines the concept of linked markers being used to indirectly select for segments of the genome associated with traits inherited in complex fashion (QTL), to select parents for breeding in other, not necessarily subsequent or contiguous generations. A process can be used for corn, soybeans, and any other plant for which markers are available and selective breeding is desired.

The efficacy of a process of this invention depends upon one or more of the inherited (genetic markers) being linked to one or more gene loci controlling expression of the phenotypic trait of interest. In addition, alleles at the marker loci and alleles at the loci controlling expression of the phenotypic trait of interest are preferably in linkage disequilibrium (Lande and Thompson, 1990). Only marker loci with contrasting parental alleles are relevant to the process.

1. Numerically Representable Phenotypic Trait

Units or factors that segregate when passing from parents to offspring exhibit the behavior expected of a single gene. The detectable appearance (phenotype) of an organism results from expression and interactions of genes with the environment. A phenotypic trait is a particular such detectable characteristic. As used herein, a phenotypic trait is a trait that is detectable and describable after visual inspection, measurement, or analysis by chemical, biochemical, or molecular techniques. A phenotypic trait is produced by the interactions of the genotype with the environment in which the plant develops. Selection based on phenotype is only effective in altering traits in offspring if it changes the frequency of genes (the heritable factors) in the population under selection. Success in a traditional breeding program is thus a function of how closely the phenotype reflects the genotype. As used herein, the term "numerically representable phenotypic trait" means a phenotypic trait that is susceptible to numerical description. That is, a phenotypic trait is quantitative or capable of being converted to a quantitative scale. Exemplary such traits include yield, stalk strength, root strength, grain quality (oil quantity and quality, starch quantity and quality, amino acid and protein composition, vitamin composition, pigment, hardness, corn gluten meal and feed quality and quantity), disease resistance (including mycotoxin producing organisms, virus resistance, fungal resistance, bacterial resistance), stress resistance (including drought, chilling, freezing, high temperature, salt, oxidative), insect resistance, herbicide resistance, physiological plant characteristics (including seed drydown, standability, "stay green"), improved nutrient utilization, and male sterility.

Some phenotypic traits are directly correlated with single gene segregation; that is, the genetic transmission from parent to offspring is reflected in phenotypic similarity. These are referred to as Mendelian, single locus, or single gene traits. Other traits do not show such direct links. Traits that fit in the latter category include those that are representable in numeric terms and show a continuous distribution when population values (X) are graphed (See FIG. 7). Such traits are referred to as "quantitative" or "continuous." Those traits typically show a continuous distribution of values in a population, and are said to be under the control of QTL.

Formation of a phenotypic database by quantitatively assessing one or more numerically representable phenotypic traits can be accomplished by making direct observations of such traits on progeny derived from artificial or natural self-pollination of a sample plant or by quantitatively assessing the combining ability of a sample plant. Combining ability is assessed, as is well known in the art, by cross-breeding each sample of plant with a tester line (a standard parental plant line having well known characteristics).

The general combining ability (gca) of a particular sample is determined by its average performance in a series of hybrid combinations. General combining ability predominantly measures additive genetic effects. Specific combining ability (sca) refers to the performance of two particular inbreds in a specific cross. Specific combining ability provides an estimate of nonadditive types of gene interactions. Some lines are evaluated directly without progeny testing.

By way of example, a plant line is crossed to, or by, one or more testers. Testers can be inbred lines, single, double, or multiple cross hybrids, or any other assemblage of plants produced or maintained by controlled or free mating, or any combination thereof. (A review and citation of pertinent literature regarding the techniques and purposes of testcrossing of early generation testcrossing in particular, and of indirect selection can be found in: Hallauer and Miranda, 1981; Hallauer, et al., 1988.) For some self-pollinating plants, direct evaluation without progeny testing is preferred.

The parental lines, and all descendants from the seminal $F_1$ hybrid between the two lines, phenotypically display, or can be induced or manipulated to display, one or more preferably codominant genetic markers that are heterozygous in the $F_1$ generation and whose phenotypic expression is for all practical purposes not influenced by environmental effects. The marker genotypes are determined in the testcross generation and the marker loci are usually mapped de novo even if a prior map exists in order to ensure that anomalies in inter-marker linkages peculiar to the population being scrutinized are taken into account in the evaluation process. De novo mapping, though usually routinely done in practice, is strictly necessary only if single or multiple marker interval methods are to be employed in the application of the invention.

Basically, a purpose of the testcross when used in a process of the present invention is to evaluate the combining ability (hybrid performance capabilities) of the sample plant or line. Inbred line testers are those now most commonly used in practice. Research has indicated that testcross results from utilization of a single inbred tester are generally applicable in prediction of crosses to other inbred lines (cf. Hallauer and Miranda, 1981, pp. 292–294). One of the important features of testcrossing is that if epistasis is not important, alleles at the QTL behave in a codominant fashion; that is, in the same manner as codominant markers.

Testcrosses are assessed for a phenotypic trait of interest in a suitably designed field trial grown at one or more locations for one or more years. Such trials are conducted by measuring values of plants grown in specific "blocks" to control variance due to environmental factors such as soil type, drainage, soil water holding ability and the like. Trials are replicated to the extent necessary to control for plot error variance.

2. Inherited Marker

A sample first plant population is genotyped for an inherited genetic marker to form a genotypic database. As used herein, an "inherited genetic marker" is an allele at a single locus. A locus is a position on a chromosome, and allele refers to conditions of genes; that is, different nucleotide sequences, at those loci. In diploid organisms, there are two alleles at each locus. These may differ in their nucleotide sequence, wherein they are said to be heterozygous, or they may have identical sequences (homozygous). For single locus controlled traits, with little or no variation due to environmental effects, phenotypic selection is effective and leads to direct and rapid concentration of selected alleles in descendent plants.

Although an inherited marker can be inherited in a dominant fashion, where the first plant population is heterozygous, an inherited genetic marker used in a process of the present invention is preferably inherited in codominant fashion so that the presence of both alleles at a diploid locus is readily detectable and free of environmental variation, i.e., their heritability is 1. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence. Heterozygosity refers to different conditions of the gene at a locus.

A genotypic database formed from a quantitative assessment of one or more inherited genetic markers is a "fingerprint" of the genetic complement. It does not present the entire complement, but a sufficient segment to facilitate identification. For purposes of this invention, inherited genetic markers are preferably distributed evenly throughout the genome to increase the likelihood they will be near a QTL of interest. One of the uses of markers in general is to exclude, or alternatively include, potential parents as contributing to offspring. Exemplary inherited markers that can be used for purposes of this invention include restriction fragment length polymorphisms (RFLPs), isozymes, and polymorphic segments of DNA, which segments have been amplified typically by the polymerase chain reaction.

One of the most useful classes of markers are RFLPs, fragments of nucleic acid sequences differing in length and consequently, in molecular weight. Such fragments can be separated by techniques sensitive to molecular weight differences; e.g., agarose starch gel electrophoresis. RFLPs are produced by restriction endonucleases that cut at specific nucleic acid sites to produce specific fragments. At least one hundred of these enzymatic, bacterially derived, "scissors" exist. Most are available commercially. Genetic linkage maps have been constructed which have located over 180 RFLP loci on 10 maize chromosomes (Helentjaris, et al., 1986). In FIGS. 4A, FIG. 4B, FIG. 4C, FIG. 4D, FIG. 4E, FIG. 4F, FIG. 4G, FIG. 4H, FIG. 4I, FIG. 4J, FIG. 4K, FIG. 4L, FIG. 4M, FIG. 4N, FIG. 4O, FIG. 4P, a maize RFLP linkage map is shown. The horizontal lines denote the chromosomes, and numbers above the lines denote the RFLP loci. For situations where the exact location of a locus is unknown, this ambiguity is denoted as an underlined segment. Loci along the right side of the figure have been assigned to chromosomes by monosomic analysis, but linkage data are not available. Loci in brackets were determined by morphological markers or isozymes, while all other loci were detected by RFLP analysis. The region which must include the centromere of each chromosome is indicated with a dashed line. About 150 RFLP markers are available for soybeans (Keim, et al., 1990).

Isozymes are variations in the structure of enzymes determined by chromatography (Tanskley, Sprague, and Orton, 1983). Isozymes are appropriate for this invention, limited only by the extent they are polymorphic in the plant of interest. For example, although at least 20 isozymes have been identified in maize, only about half of those are informative in any cross involving commercially useful inbred lines.

Other markers include amplified polymorphic DNA segments. (Lee et al., 1990; Williams et al., 1990). Amplification can be achieved, for example, by the polymerase chain reaction. An in vitro method for primer-directed enzymatic amplification of DNA sequences has been developed (U.S. Pat. No. 4,683,202). The polymerase chain reaction (PCR) has made it possible to take and multiply DNA sequences in exponential fashion to produce amounts amenable for further analysis, including nucleic acid sequencing or identification by specific nucleotide probes. Prior to the PCR approach, the analysis and identification of specific nucleic acid sequences were hampered by difficulties in detecting or working with extremely small amounts of DNA, particularly those extracted from natural tissue samples.

The development of the PCR overcame some of the prior limitations in this field by producing selective enrichment of specific DNA sequences. Applications of PCR have been numerous and have been useful in many fields, e.g., analytical molecular biology and clinical diagnosis. PCR has been used to prepare material for nucleotide sequence analysis, analysis of chromosomal rearrangements, cloning of cellular and viral genomic sequences and for detection of vital pathogens.

Basically, the method of PCR amplification involves use of two oligonucleotide primers flanking the DNA segment to be amplified. Repeated cycles of heat denaturation of the DNA followed by annealing of the primers to their complementary sequences at low temperatures, and extension of the annealed primers with DNA polymerase, comprise the major part of the methodology. The primers hybridize to opposite strands of the DNA target sequences. Hybridization refers to annealing of complementary DNA strands, where complementary refers to the sequence of the nucleotides such that the nucleotides of one strand can bond with the nucleotides on the opposite strand to form double stranded structures. The primers are oriented so that DNA synthesis by the polymerase proceeds bidirectionally across the nucleotide sequence between the primers.

This procedure effectively doubles the amount of that DNA segment in one cycle. Because the PCR products are complementary to, and capable of binding to, the primers, each successive cycle doubles the amount of DNA synthesized in the previous cycle. The result of this procedure is exponential accumulation of a specific target fragment, that is approximately $2^n$, where n is the number of cycles.

After the DNA is amplified, it is customary to verify that the amplified DNA is indeed the DNA targeted for amplification. A commonly used method of detection of specific nucleic acid sequences is electrophoretic separation of the products of amplification in a semi-solid gel, denaturation and transfer of the electrophoretically separated products to a solid substrate, labelling a probe with a radioactive label, adding the probe to the solid substrate containing sequences to be identified, and then checking for the presence of label in the amplified DNA-probe hybrids. Radioactive probes are most usually employed, for example, $P^{32}$.

If a labelled probe is complementary to the test sequence, hybrids will form. In DNA, there are four base pairs—adenine (A), guanine (G), thymidine (T), and cytosine (C)—A pairs with T, G with C. In RNA, T is replaced by uracil (U). Detection of radioactive probes requires exposure of film to the radioactive signal for a period of time, then developing the film. This process may take days or weeks, rendering it unsuitable for rapid clinical diagnosis. Non-radioisotopic labels are alternatives which eliminate the need for autoradiography. Those labels require specific detectors as is well-known in the art.

For purposes of this invention, inherited marker genotypes are converted to numerical scores, e.g., if there are 2 forms of RFLP, A and B, at a particular locus using a particular enzyme, then diploid complements converted to a numerical score, for example, are AA=2, AB=1, and BB=0; or AA=1, AB=0 and BB=−1. The absolute values of the scores are not important. What is important is the additive nature of the numeric designations. The above scores relate to codominant markers. A similar scoring system can be given that is consistent with dominant markers.

The number of inherited markers necessary to develop a total marker score value that adequately reflect genotypic content has been estimated by Lande and Thompson (1990). For markers randomly distributed across the maize genome, a minimum number is about 40. Of course, if the experimenter has prior knowledge of marker linkages with loci controlling important traits, fewer are needed.

Inherited markers are preferably limited to those that are sufficiently polymorphic to permit discrimination among genotypes (that is, are "informative"). All need not be significantly associated with the phenotypic expression of the traits determined in the testcross generation. Empirically, it was not found necessary to select among the markers based on degree of association. However, if cost is a factor, lab determinations may be reduced by only including markers with some predetermined probability level of association, e.g., a t-test probability level of 0.15. A process can be extended over multiple loci by using multiple regression to estimate regression coefficients for a group of marker loci.

In one embodiment, genotyping is performed on at least one generation of a descendant line for which the numerical value of the quantitative trait or traits of interest are also determined. Because marker alleles are not directly associated with the QTL to be selected, the nature of an association varies in different populations. Consequently, a specific set of markers and their QTL associations most likely apply only within genetically related lines.

3. Evaluating an Association Between a Numerically Representable Phenotypic Trait and an Inherited Genetic Marker A formed phenotypic and genotypic database are evaluated to define an association between at least one numerically representable phenotypic trait and at least one inherited genetic marker. Preferably, that association is expressed in a form whereby the phenotypic trait is a function of an inherited genetic marker.

a. Seminal Hybrid

In one embodiment, a plant for which a prediction of phenotypic trait occurrence is being made (a second plant) is from an advanced selfed generation of a seminal $F_1$ hybrid and the plant population used for phenotypic and genotypic database formation (first plant) are from a descendant generation of that $F_1$ hybrid. A seminal hybrid can be produced by a variety of means well known in the art. In an exemplary means, two essentially homozygous (characterized by an inbreeding coefficient of about 0.95 or greater) inbred lines (parent "a" and parent "b") are crossed to produce an $F_1$ hybrid (FIG. 3) termed the "seminal hybrid."

A number of $F_n$ generation lines within $F_m$ individuals ($F_n(F_m)$) where $m = 2 \ldots, \infty$; $n = m, m+1, m+2, \ldots, \infty$, are produced by self-pollination using standard techniques well known in the art. Such subsequent generations are designated herein as $F_m$ where m is 2 to n generations. The first selfed generation after $F_1$ is $F_2$. Generations occurring after any specified reference generation is termed an "advanced generation". Any generation occurring before a specified generation is termed an "earlier generation".

Figure 3:
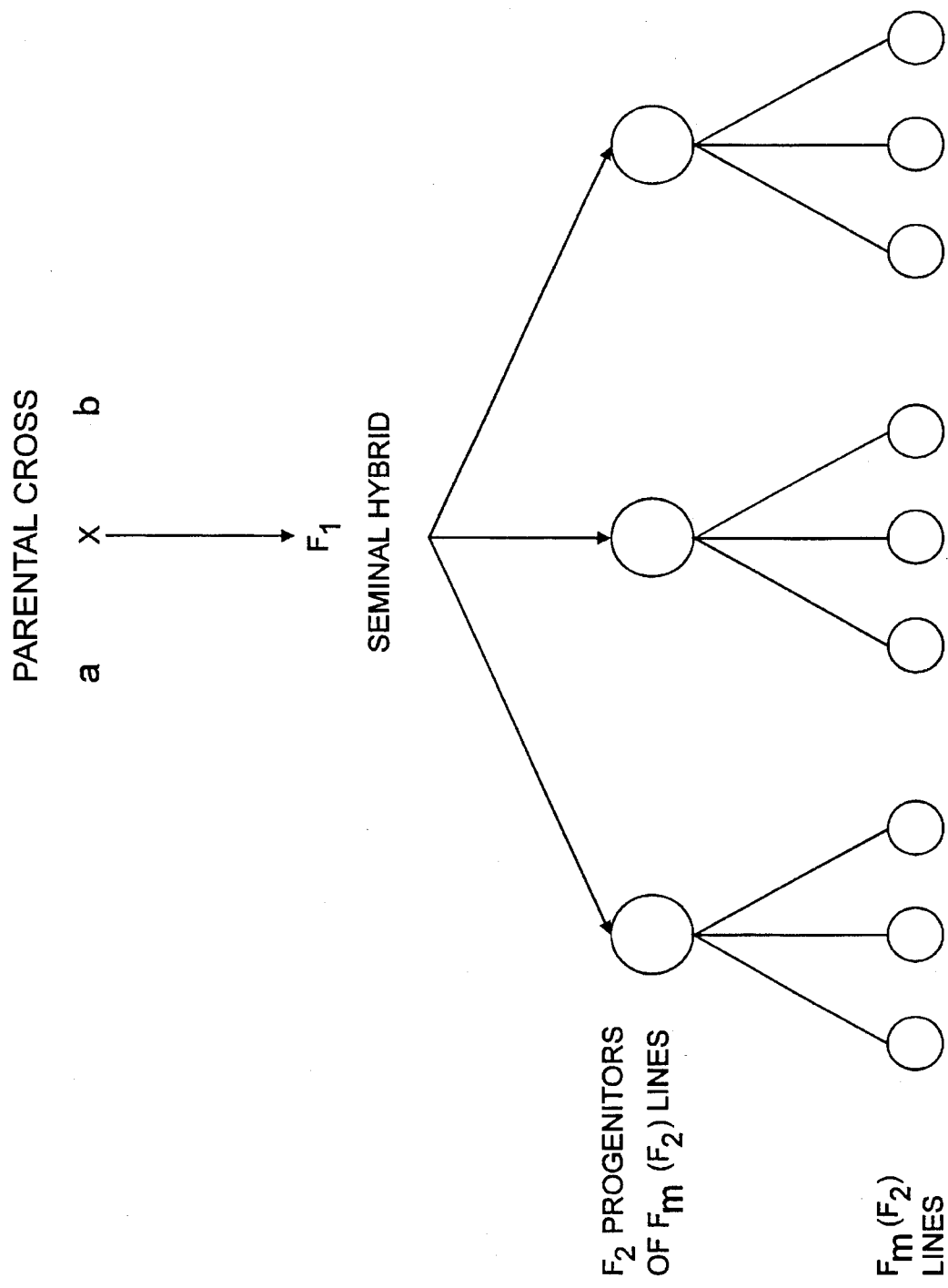
FIG. 3 is a pedigree flow chart of the general breeding scheme used in this invention.
Figure 4A:
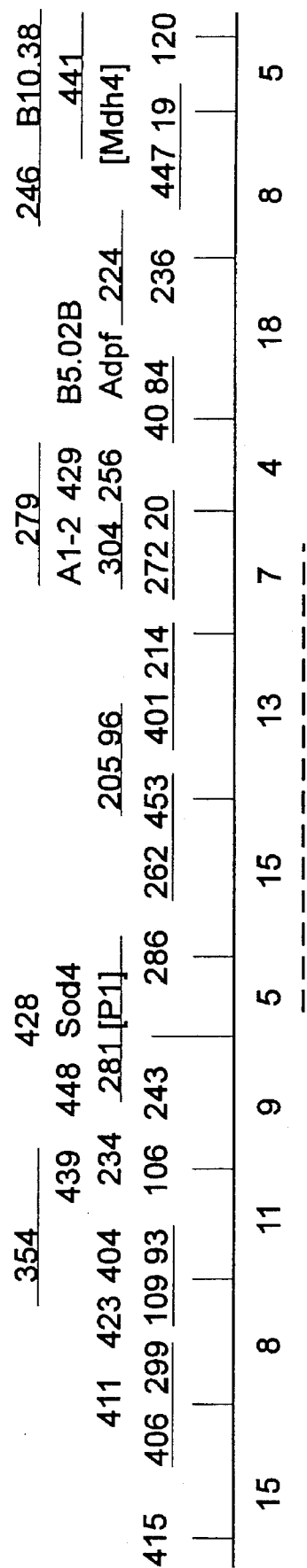
Figure 4B:
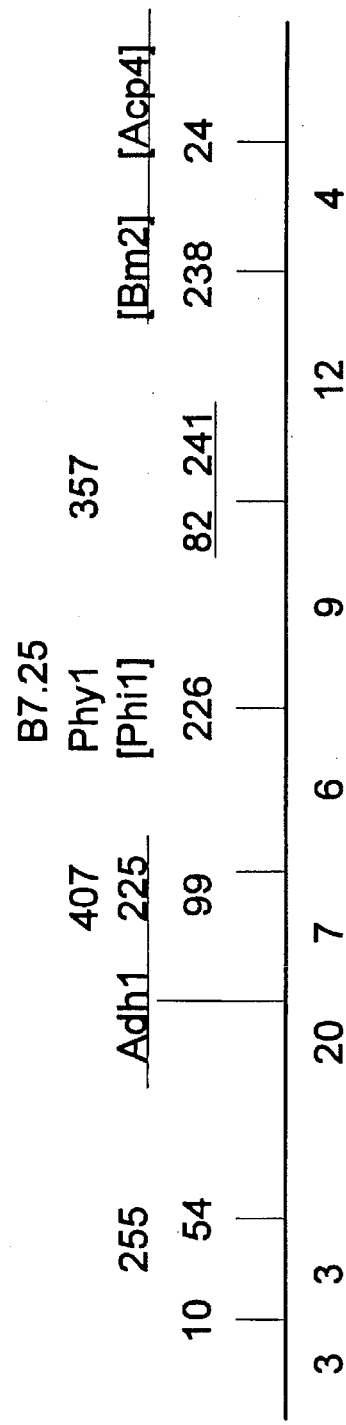
Figure 4C:
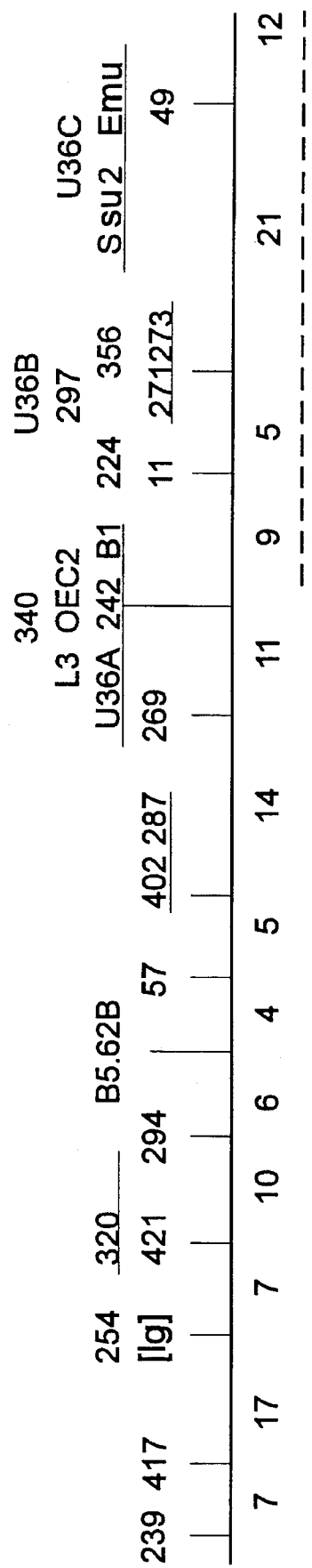
Figure 4D:
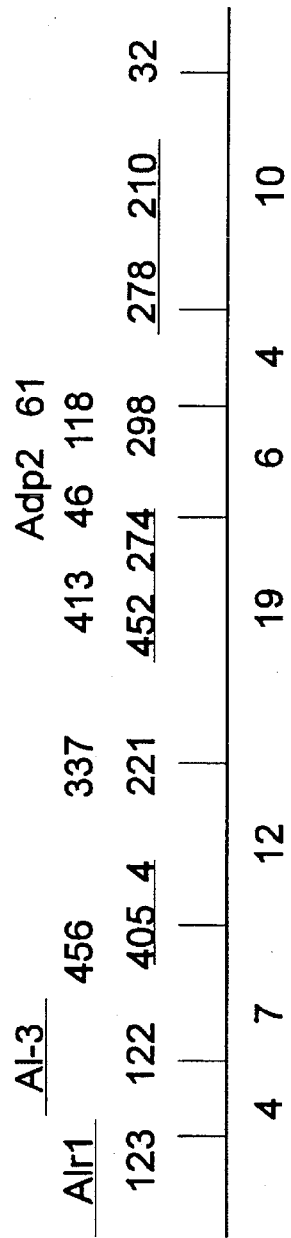
Figure 4E:
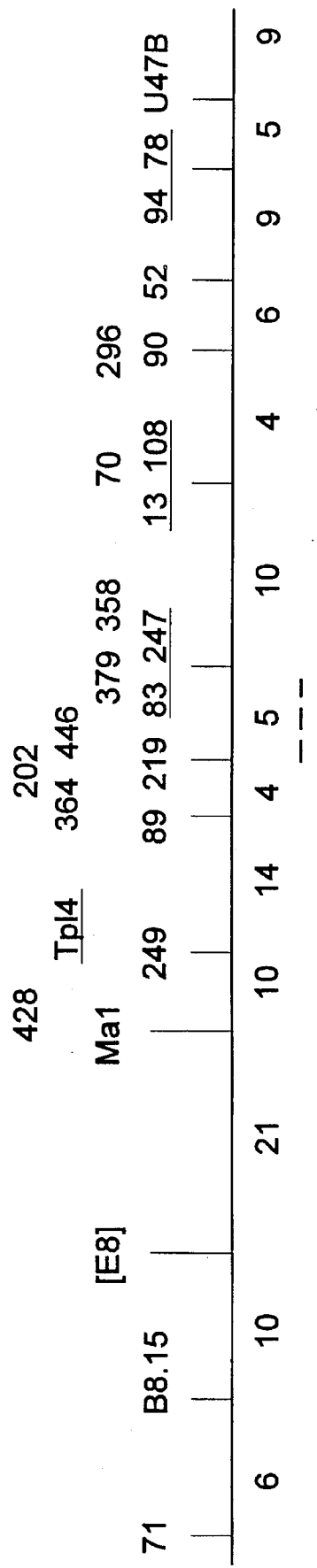
Figure 4F:
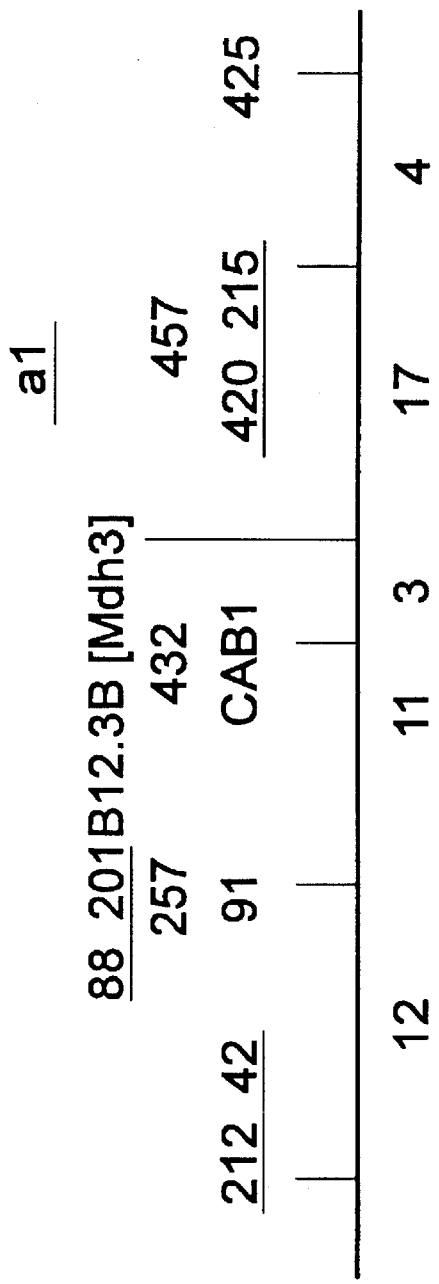
Figure 4G:
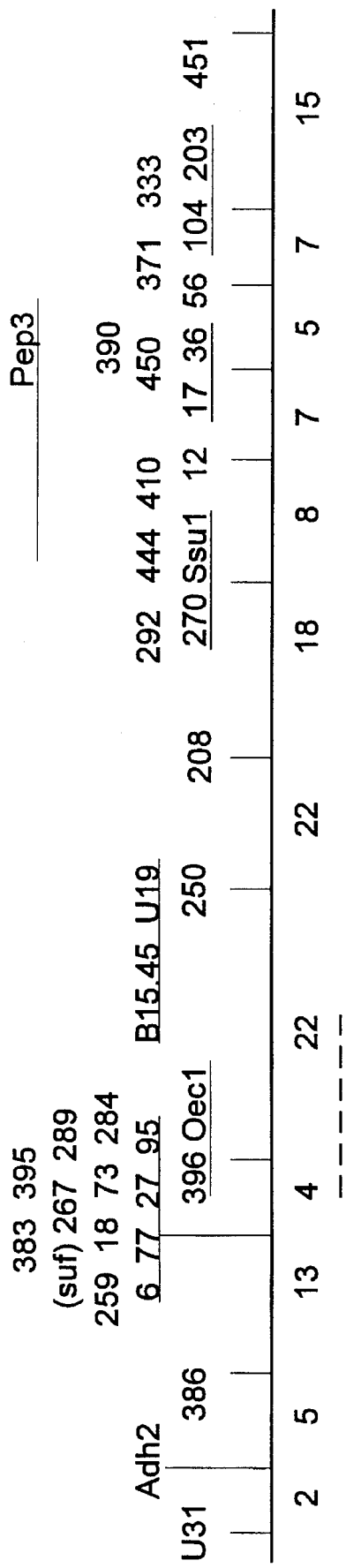
Figure 4H:
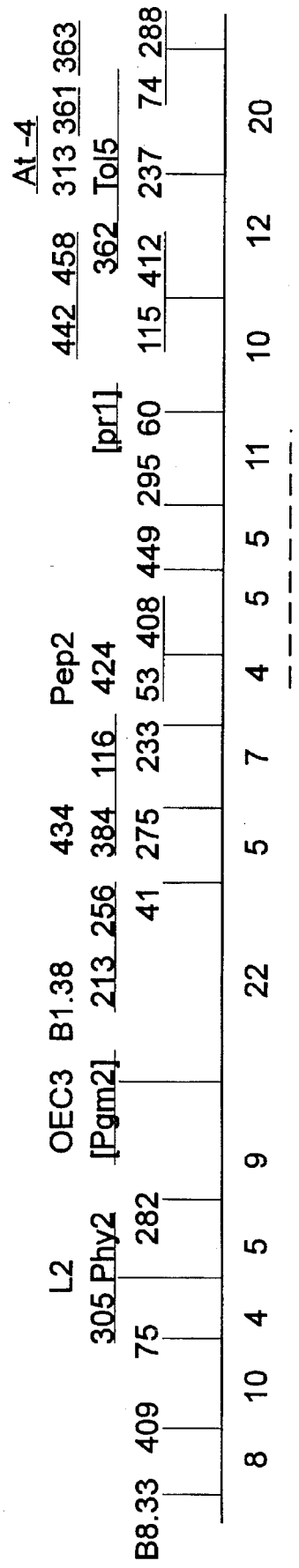
Figure 4I:
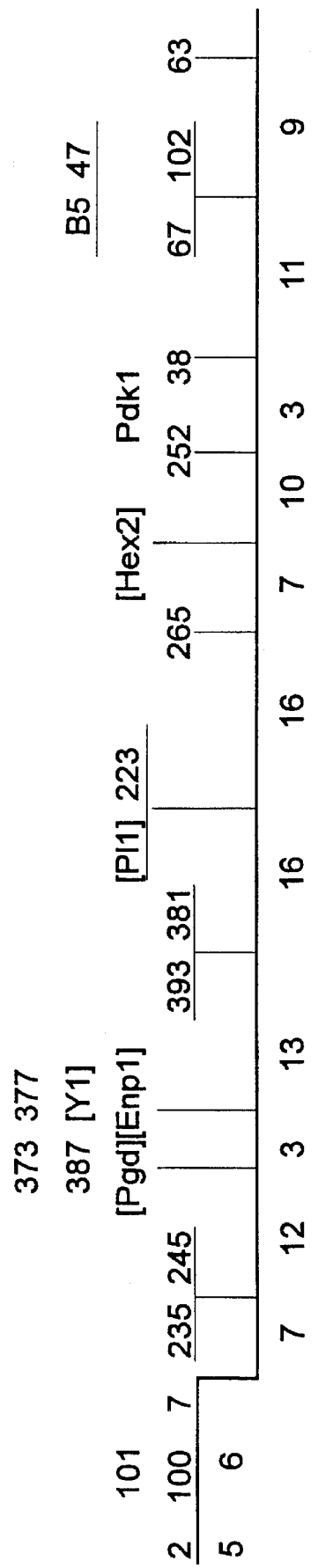
Figure 4J:
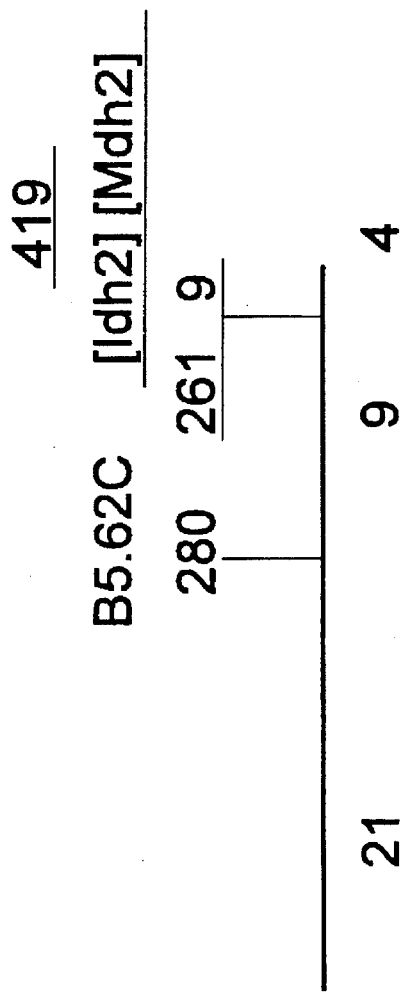
Figure 4K:
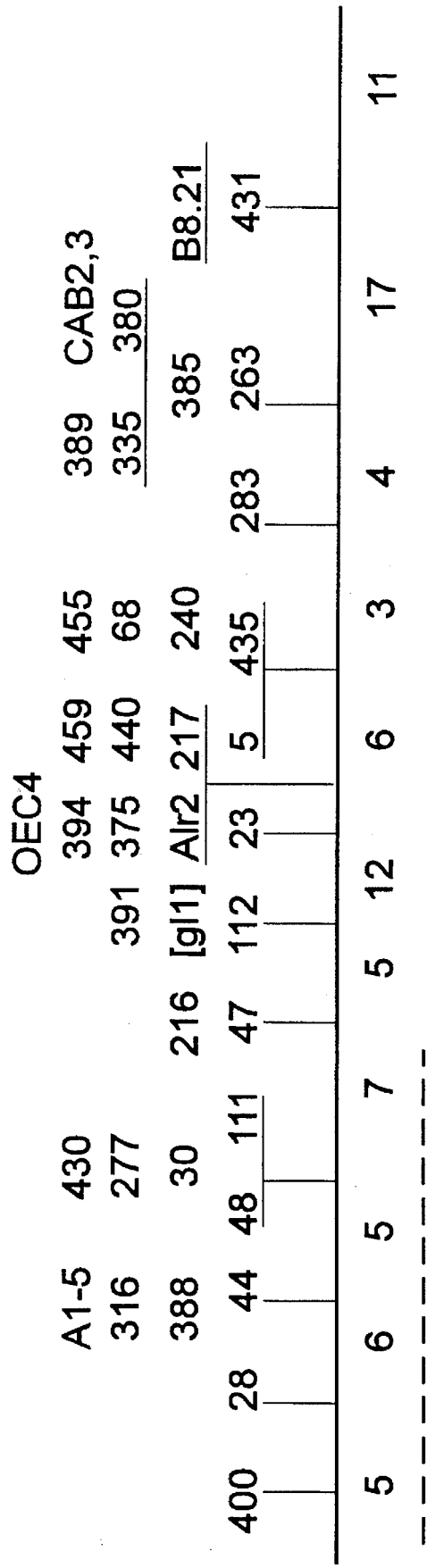
Figure 4L:
Figure 4M:
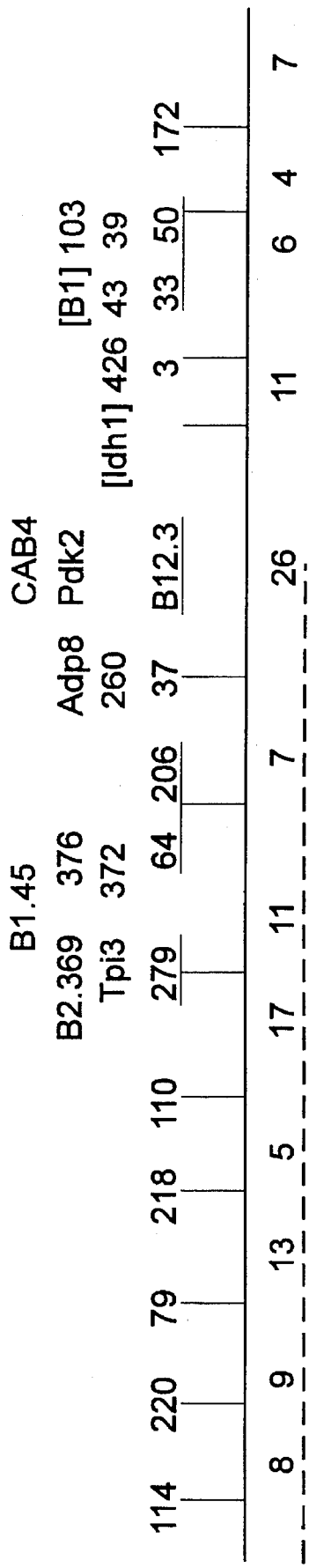
Figure 4N:
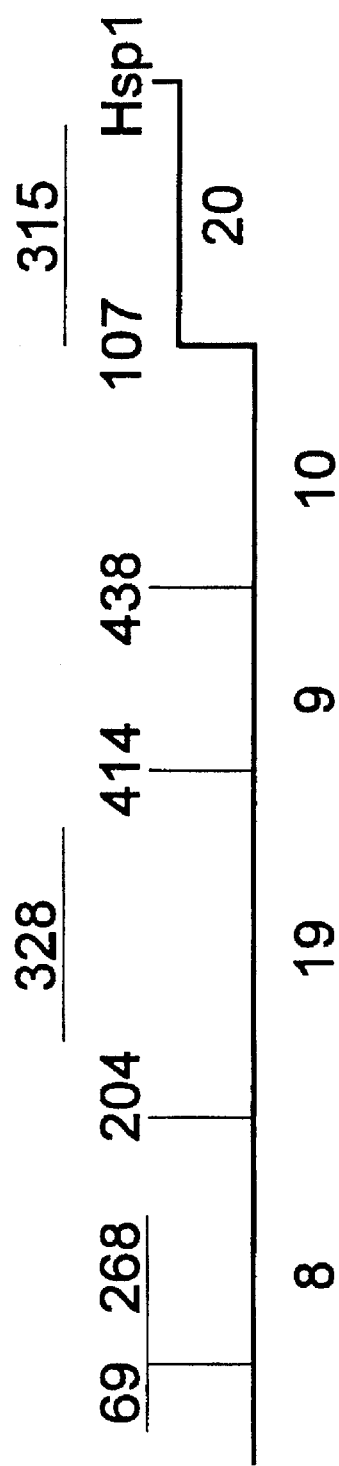
Figure 40:
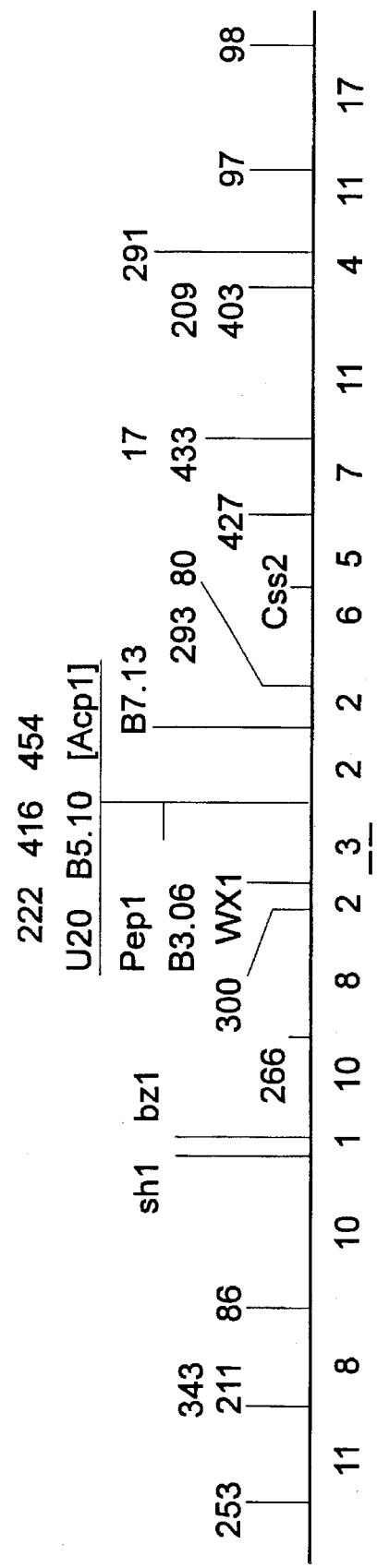
Figure 4P:
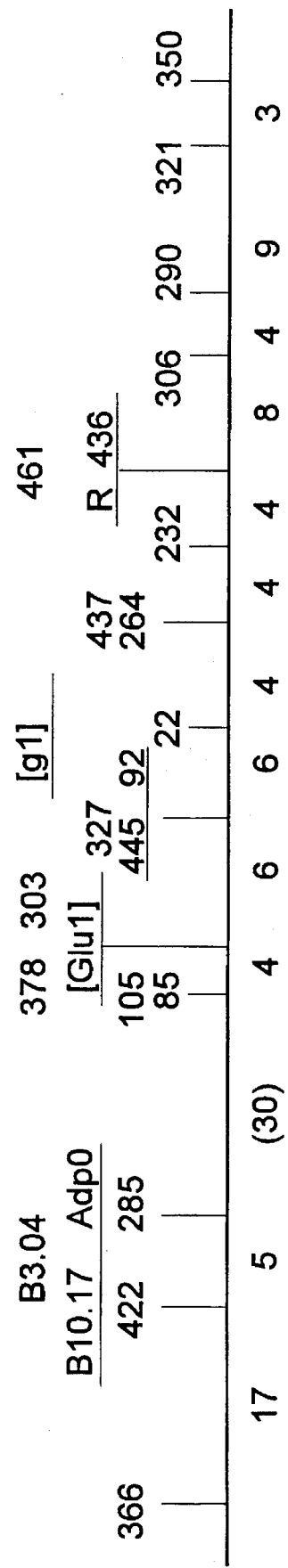
Figure 5A:
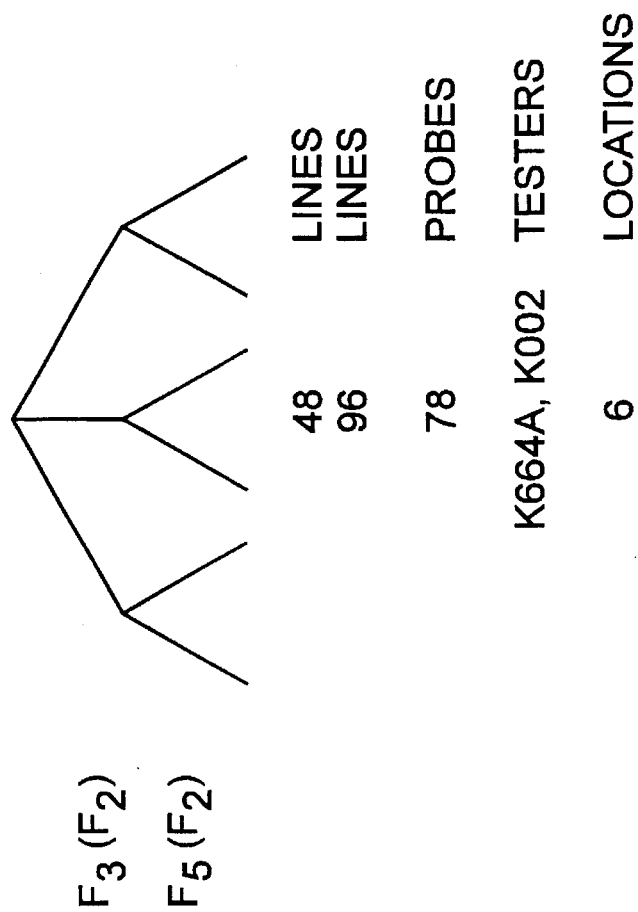
FIG. 5A and FIG. 5B are an experimental design of a selective breeding experiment using a method of this invention (Example 1).
Figure 5B:
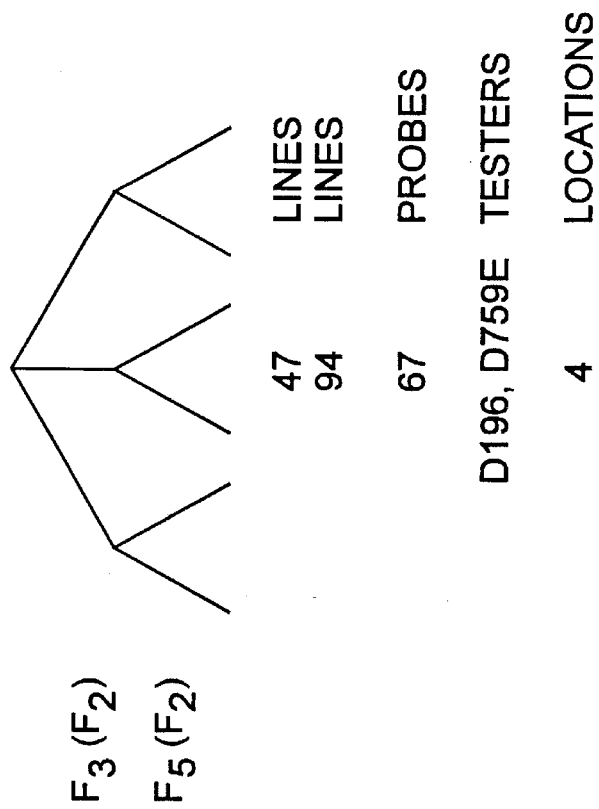

Preferably, in accordance with this embodiment, a first plant population used for formation of a phenotypic and genotypic database and for definition of an association is from the first or second generation after that seminal $F_1$ hybrid. More preferably, a sample is an $F_3(F_2)$ or $F_2(F_2)$ line, where an $F_3(F_2)$ "line" refers to bulked progeny produced by the self-pollination of a single $F_2$ individual and an $F_2(F_2)$ "line" refers to a single $F_2$ individual itself. The plants which are the founding nodes in the pedigree that relate to each line are called "progenitors" (FIG. 3).

As set forth above, formation of a phenotypic database by quantitatively assessing one or more numerically representable phenotypic traits can be accomplished by making direct observations of such traits on progeny derived from artificial or natural self-pollination of the sample or by quantitatively assessing the combining ability of the sample.

As set forth above, a genotypic database is formed on those same first population plants. By way of example, $F_n(F_m)$ lines are scored for the presence or absence of the parental allelomorphs of each of the inherited markers. In the case of m=n, the $F_n$ individuals are themselves scored. For n> m, the marker score of each $F_n(F_m)$ line is obtained by scoring a random sample of about at least six individuals: if all individuals sampled carry the same parental allelomorph, the line is scored as being homozygous for the allelomorph; if not, the line is scored as being heterozygous.

A marker score is expressed in a numeric form consistent with codominant expression. For example, a marker score consistent with one of the parental allelomorphs can be given a numeric value of 1.0; a marker score consistent with the opposite parental allelomorph is then given a value of −1.0; while a marker score consistent with a heterozygote is then given a value of 0. The scale and rankings in numeric value with respect to parental origin remain consistent across all marker loci. As the markers are genetic in nature, each has a single definite location in the genome.

The genetic marker and phenotypic trait data are evaluated and an association between at least one genetic marker and at least one phenotypic trait is defined. Preferably, that association is expressed as a regression equation with the phenotypic trait as the dependent variable and the inherited genetic marker as the independent variable. A regression coefficient is estimated between at least one quantitatively described phenotypic trait and at least one marker locus in the generation evaluated either directly or by testcrossing. For this purpose, values of individual phenotypic traits for a plant or bulked progeny of a plant are determined. Bulked progeny are the collective progeny from the same generation that are descendants of a single plant. Those values are expressed as a number on a continuous scale.

For each plant, a marker determination is made. By way of example, let the symbol $Y_i$ be used for the value of the quantitative phenotype of the $i^{th}$ plant, or its bulked progeny, wherein each Y represents the numerical value of the plant, or its bulked progeny, for a trait of interest on a continuous scale, and let the inherited genetic marker score at a locus of that plant, or its bulked progeny, be expressed as $X_i$. Evaluating the association between $Y_i$ and $X_i$ over many plants, or families of bulked progeny, provides an estimate of the regression coefficient, b for that locus (See Equation [1] below).

$$Y_i = bX_i + e_i \ (i=1, 2, \ldots, n) \quad [1]$$

where n=the total number of plants or families o bulked progeny.

The regression coefficient expresses the average unit change in $Y_i$ for a unit change in $X_i$. In practice, means (average values) and standard deviations of the quantitative traits are also computed.

In a preferred embodiment, a plurality of phenotypic and genotypic values are formed by quantitatively assessing and genotyping a sample of plants for a plurality of numerically representable values of phenotypic traits and inherited genetic markers. Where a plurality of trait and marker values are employed, a relationship and, preferably a regression equation is determined. Thus, each numerically representable phenotypic trait is evaluated for its relationship to a number of inherited genetic markers and a regression equation can be expressed for that phenotypic trait.

One such equation is preferably of the form shown in Equation [2] below.

$$Y_i = \mu + \sum_{k=1}^{t_j} \beta_{jk} X_{ijk} + \epsilon_i \quad [2]$$

where $Y_i$=mean performance of the trait, or a linear combination of the traits, of interest of the $i^{th}$ $F_n(F_m)$ line (i=1, 2, ..., l);

$\mu$=the mean value of the dependent variable;

$\beta_{jk}$=coefficient of the regression of Y on the $k^{th}$ marker locus in the $j^{th}$ group of markers (j=1, 2, ..., s; k=1, 2, ..., $t_j$);

$X_{ijk}$=numeric value of the $k^{th}$ marker in the $j^{th}$ group of markers for the $i^{th}$ $F_n(F_m)$ line; and $\epsilon_i$=deviation from regression for the $i^{th}$ $F_n(F_m)$ line.

In the above formulation, the magnitudes of l, s, and $t_j$(j=1, 2, ..., s) are arbitrary.

During, or subsequent to, an evaluation outlined above for the $F_n(F_m)$ lines, a number of $F_x$ generation (x≥n) individuals from the original seminal $F_1$ hybrid are obtained by successive generations of self-pollination. The method is very flexible. Generally, lines are set up, their performance is evaluated, and their performance in advanced generations is estimated by marker genotype in terms of total marker score by means of the regression equation [2]. Those individuals can be descendants of the $F_m$ progenitors of the $F_n(F_m)$ lines (being, though, in all cases descendants of the seminal $F_1$ hybrid) used in the evaluation outlined above.

In the case that the $F_x$ generation individuals are descendants of the $F_m$ individuals used in the evaluation outlined above, they can be, but are not necessarily, direct descendants of the $F_n$ individuals used in the evaluation. If the $F_x$ individuals are direct descendants of the $F_n$ individuals, the $F_n$ individuals would necessarily have been simultaneously self-pollinated and crossed as males to the tester(s); but, if the $F_x$ individuals are not descendants of the $F_n$ individuals they necessarily would be descendants of other members of the same $F_n(F_m)$ (n>m) line. The $F_x$ individuals could be a mixture of descendants of $F_n$ individuals and descendants of related individuals belonging to the same $F_n(F_m)$ line. The essential point, is that $F_x$ individuals are classifiable as descendants of $F_m$ individuals. In practice, the only instances in which $F_x$ individuals would be direct descendants of $F_n$ individuals would be those for which n=m. In summary, one can have: (a) simply $F_x$ individuals; (b) $F_x(F_m)$ individuals; or (c) even $F_y(F_x(F_m))$ (y>x) lines.

The $F_x$ or $F_x(F_m)$ individuals or $F_y(F_x(F_m))$ lines are then assigned marker scores in a manner consistent with that employed in the assignment of marker scores to the $F_n(F_m)$ lines used in the testcross evaluation. Also, the marker scores are given numeric values consistent with those given to the marker scores of the $F_n(F_m)$ lines used in the testcross evaluation. A total marker score (tms) is then calculated for each $F_x$ or $F_x(F_m)$ generation individual, or $F_y(F_x(F_m))$ as shown below in Equation [3].

$$tms_v = \sum_{u=1}^{g} \hat{B}_u Z_{uv}, \left( g \leq \sum_{j=1}^{s} t_j \right) \quad [3]$$

where $\hat{B}_u$=the estimated regression coefficient estimate, and $Z_{uv}$=the marker score value of the $i^{th}$ individual at the $u^{th}$ marker locus corresponding to one of the loci out of the total of $$t = \sum_{j=1}^{s} t_j \quad [4]$$

loci used in calculating estimates of the parameters $\mu$ and $B_{jk}$ in equation [2], (v=1, 2, ..., h), for h of arbitrary magnitude. Equation [3] allows for the discarding of some estimates of regression coefficients obtained in calculation of the regression equation [2] based on a t or F test probability level; e.g., a t test with type I error probability p<0.15. That is, only markers showing a significant association with a QTL might be included.

Genetic markers can be considered individually or as groups wherein groups are defined as, for example, all genetic markers on one chromosome. All genetic markers could even be included as single group. In an illustrative embodiment, a regression equation for each individual genetic marker was calculated separately. Estimated regression coefficients were used in calculating of a total marker score for advanced generation lines in which individual regression estimates were summed over all marker loci.

Regression estimates at selected marker loci are combined to determine a total marker score (tms) for lines in the testcross generation or for any advanced generation. The regression estimates are combined by summing over all selected marker loci. Correlations can exist for genotypic values among marker loci, which might affect marker selection. In practice, individual or groups of loci are used and their regression estimates are summed.

Single or multiple interval mapping analysis can also be employed as an alternative to estimate the regressions of the trait of interest on a QTL inferred to lie on the intervals between marker loci. The regression estimates are again used to produce a tins. Maximum likelihood estimates are used to determine the probable location of QTL between markers. This is a method derived by Lander and Botstein (1989). The utility of this method increases as population size increases to about 150–200. Because estimates of recombination are required for interval mapping, 50 lines, at least, are required. The utility of the method is greater, though, if more lines are used.

It should be noted that in practice, a regression equation such as equation [1] above should be modified to include all blocking or design parameters relevant to the experimental design. Also, it should be noted that the dependent variable, $Y_i$, in equation [2] can consist of means based on the total number of sampled individuals of the $i^{th}$ line, or a fraction thereof. There are no particular proscriptions regarding experimental design. The method is not dependent on, for example, whether there are equal or unequal number of observations for each testcross. Both conditions are susceptible to adequate statistical treatment. (cf. The four types of estimable functions. Chapt. 9. SAS/STAT User's Guide, 6.03 Ed. 1988. SAS Inst., Inc. Cary, N.C.).

Under continuous self pollination, disequilibrium between linked loci as measured by the difference between the frequencies of parental and non-parental double heterozygotes (the only source of crossing over and recombination) is reduced each generation by an amount equal to $2\lambda/(1+\lambda^2)$ where $\lambda=1-2\cdot$(recombination frequency). Hence, after n generations of selfing, disequilibrium between the two loci has an expected value of $(2\lambda/(1+\lambda^2))^n$. Clearly, if the parent inbred lines that produced the $F_1$ carry divaricate alleles at a locus controlling phenotypic expression of an important trait, closely linked marker alleles will serve as indicators of probable presence of QTL in successive generations of selfing. Thus, if desirable phenotypic expression can be shown to be associated with a marker allele, or a set of marker alleles, in an early selfing generation, the same association should persist throughout subsequent generations of selfing. In short, inbreeding by selfing overpowers recombination. This expectation was confirmed in the experiments described hereinafter in Example 1.

A rapid approach to homozygosity of all loci under self-pollination acts to prevent dissipation of the linkage disequilibria due to meiotic recombination. Thus marker genotype remains strongly correlated with effects on phenotypic expression that are attributable to alleles at linked loci controlling phenotypic development of the trait. Because self-pollination tends to maintain linkage disequilibrium, and if phenotypic expression of a trait is more or less proportional to the cumulative effects of all loci involved in its developmental control, total marker scores produced by a process of this invention is likely to be a good indicator of genetic merit of advanced generation individuals or lines.

A process of this invention is useful in plant breeding because: (a) tms values are a better indication of performance in hybrid combination of the $F_x(F_m)$ individuals or $F_y(F_x(F_m))$ lines than is testcross performance of the antecedent $F_n(F_m)$ lines; (b) an index including both $F_n(F_m)$ testcross performance and $F_x(F_m)$ or $F_y(F_x(F_m))$ tms significantly enhances prediction of phenotypic trait performance in hybrid combination of $F_x(F_m)$ individuals or $F_y(F_x(F_m))$ lines beyond that provided by testcross performance of the $F_n(F_m)$ lines alone; and (c) the precision in predicted performance of $F_x(F_m)$ individuals or $F_y(F_x(F_m))$ lines afforded by tins values is sufficiently acute to allow a practical degree of selection intensity sufficient to produce a gain from selection on all $F_x$ generation individuals, regardless of $F_m$ generation progenitor, greater than that from direct phenotypic testcross selection on $F_x$ individuals descended from the seminal $F_1$ hybrids.

The efficacy of a process of this invention depends upon one or more of the genetic markers being linked to one or more loci controlling to some greater or lesser extent, phenotypic expression of the trait of interest. In addition, the alleles at a marker loci and alleles at a loci controlling phenotypic expression of the trait of interest are in linkage disequilibrium (Lande and Thompson, 1990). Because only marker loci with contrasting parental alleles are considered in a process of the present invention, and because essentially homozygous inbred lines are used to produce $F_1$ hybrids, linkage disequilibrium between any marker locus and any linked locus with contrasting alleles is at the outset ensured.

Performance in advanced generations can be predicted on the basis of probable QTL linkage with at least one marker whose functional value can be estimated in a related generation where the marker is in linkage disequilibrium with the QTL. A process of this invention provides information on the relative values of the lines in producing new hybrids with quantitative trait values of interest. Prediction of performance is extendable over years and over environments.

Increased efficiency is obtained by genotyping plants of the generation to be selected to obtain a marker profile, and combining that profile with, in an illustrative embodiment, a previous tester generation's testcross regression estimates (marker and QTL) to produce total marker scores. The testcrosses can be performed in any generation, but are preferably performed in early generations about number 2 to 3. Results from direct evaluation of plants rather than progeny tests are also suitable. Predictions have value in proportion to anteriority of testcrossing. Lines in later generations become homozygous and remain constant in subsequent generations. The total marker scores of the generation on which selection is to be performed are used to target plants for subsequent crossing to generate a new cross bred generation of hybrids. The total marker score allows selection of those plants, seeds and genomes with the most preferred performance. Performance can be predicted across years and across testers. Advanced selection is more effective the more generations skipped. Stability of lines is achieved about 4–5 generations after selfing ($F_{5-6}$).

Results contained in the examples disclosed herein demonstrate the use of this invention. There has been gain in advanced generation testcross results beyond that achievable by selection for early testcross values alone. In particular, this outcome has been shown for yield, one of the most commercially valuable, yet elusive, phenotypes. Greater efficiency is achieved by selection on the basis of individual plants, achieving the same level of accuracy of other selection schemes requiring many plants. Other numerically representable traits for which the methods of this invention are applicable include stalk strength, root strength, insect and disease resistance.

An additional benefit of the method of marker scores for improved breeding programs disclosed herein is that marker genotypes may be determined in a nondestructive manner permitting the sample plant to produce progeny for subsequent generations.

Selection can be practiced on inbred lines or on hybrids resulting from crosses of inbred lines. For example, maize is normally cross-pollinated, which perpetuates genetic variability; therefore, artificial control is necessary to effect inbreeding which is aimed at production of genetic uniformity. Many methods of control have been developed, one of which is to cover the developing ear shoot, before silks have emerged, by a small bag. After the silks emerge, the tassels containing the male pollen are bagged and transferred to the silks (stigma) of the maternal plant.

Self-fertilization is the preferred method of inbreeding in plants which are able to reproduce in this manner. Selection of parents based on their phenotypes is a method used to direct the development of the offspring lines toward desirable phenotypes. Unfortunately, reduction in vigor and infertility accompanies inbreeding.

b. No Seminal Hybrid

In another embodiment, a process of the present invention can be used where a second plant in which a prediction of phenotypic value is to be made and a first plant population sample on which the phenotypic and genotypic databases are formed are not derived from a common seminal hybrid. The only limiting relationship between that plant and the sample population is that both are members of the same general population of genotypes.

In accordance with such a process, a phenotypic and genotypic database are formed on a first plant population. Database formation is accomplished as set forth above. Those databases are evaluated to define an association between a numerically representable phenotypic trait and an inherited genetic marker(s). In a preferred embodiment, a plurality of phenotypic traits and inherited genetic markers are used.

A marker score is based upon the degree of inherited marker incongruence between genotypes of the parents of a given hybrid plant. Quantitative weights, derived from the coefficients of regression of the plurality observed values relating to a single phenotypic trait of interest, are applied to the parental inherited marker variables of the hybrids represented in the data to be predicted. The parental inherited marker incongruence variables are derived as functions of numerically constituted copy number representations of the inherited marker alleles constitutive to the marker loci of all parental genotypes under consideration.

The methodology developed for generalized prediction is an adaptation and extension of that outlined by Allen (1971, 1974); Wahba and Wold (1975); and, particularly, Golub, Heath and Wahba (1979) and is complaisant to any type of genetic marker.

The predictor variables in the prediction model are based upon the degree of genetic marker incongruence between the parental genotypes of the putative hybrids. Quantitative weights applied to the predictor variables are supplied by the coefficients of the regression of observed values of hybrid performance, calculated from a suitably constructed predictor data base, on the parental genetic marker incongruence variables of the hybrids represented in the data to be predicted. The prediction model is simply a regression equation with the independent variables being genetic incongruence between parental genotypes. The parental genetic incongruence variables are derived as functions of numerically constituted copy number representations of genetic marker alleles constitutive to marker loci of all parental genotypes under consideration. An outline of a preferred process follows.

Let g1 be a row vector specific to a parent of a hybrid with components consisting of marker allele genotypes, and let g2 be a similarly constituted row vector specific to the opposite parent. Each component of the vectors corresponds to a specific marker allele, and the order (total number of components) of each vector equals the total number of marker alleles incident to all marker loci of all parental genotypes under consideration. Any particular vector component will have a value of 2, 1, or 0 depending on the number of copies of the corresponding marker allele present at the appertaining locus of the parental genotype in question. Denoting g1#g2 as the elementwise, or Hadamard, product of g1 and g2, and h as a continuous scalar variable with domain $0 \leq h \leq 1$, a function g=(g1+g2)−(g1#g2)·h provides a row vector of values based on genetic incongruence of the parental genotypes, with the value of h providing the degree of emphasis to be placed upon heterozygosity (incongruence of the parental genotypes) in the prediction model. When h=1, only those components of g corresponding to alleles at heterozygous loci receive non-zero values. When h=0, the components of g receive values equal to the number of copies of the corresponding alleles present at the appertaining loci. When h=0.5, alleles present in single or double copies receive equal weight, i.e., homozygotes and heterozygotes are equally weighted. In essence, a breeder chooses the degree to which heterozygosity/homozygosity receives emphasis in the prediction model by choice of the value of h along the continuum $0 \leq h \leq 1$.

If the genetic markers employed do not permit ascertainment of copy number (single primer DNA amplification, for example), a comparable degree of emphasis on heterozygosity/homozygosity is obtained by choice of h along the continuum $0 \leq h \leq 2$, with h=2 representing total emphasis on heterozygosity. The vectors, g, of a set of hybrids are then displayable in matrix form, each row of the matrix consisting of the particular vector, g, of a specific hybrid.

Let X be a matrix as such, with dimensions n×m, and let Y be a corresponding n×1 vector of observed values of the n hybrids in question. Assume that the components of Y are distributed independently $(\mu_i, \sigma^2)$, i=1, 2, ..., n; and further assume that all variables in X and Y are expressed in terms of deviations from their respective means. By the singular value decomposition of X, $$P_\kappa = XV_\kappa L_\kappa^{-\frac{1}{2}} \quad (\kappa \leq m), \qquad [5]$$

where $L_\kappa$ is a κ×κ diagonal matrix of κ positive eigenvalues of X'X or XX', and $P_\kappa$ and $V_\kappa$ are matrices whose columns are the κ eigenvectors of XX' and X'X, respectively, corresponding to the eigenvalues arrayed in $L_\kappa$. The dimensions of $P_\kappa$ and $V_\kappa$ are n×κ and p×κ, respectively.

For the model $$Y = P_\kappa \theta + R + E, \qquad [6]$$

where $R = U - P_\kappa \theta$ for E(Y)=U, Y=a vector of n observed values, θ=a vector of κ regression coefficients, and E=an n-vector of random errors, the least squares estimate of θ obtained from n-observation data (data consisting of n observations) is $$\hat{\theta}_n = P'_\kappa Y \qquad [7]$$
$$= L_\kappa^{-1/2} V_\kappa X'Y.$$

Let x be a row vector of independent variables corresponding to a future predicted observation, and let y be the corresponding value of the future observation. Consistent with the definitions of Y and X, y and the components of x are expressed as deviations from the means of the variables of Y and X, respectively.

Let $^X\!/_x$ denote an augmented matrix of independent variables obtained by appending x to X. By application of the linear transformation implicit in Equation [5], $$\rho_\kappa = xV_\kappa L_\kappa^{-\frac{1}{2}} \qquad [8]$$

$$\left( \frac{P_\kappa}{\rho_\kappa} \right) = \left( \frac{X}{x} \right) V_\kappa L_\kappa^{-1/2}.$$

Then, $$(P'_\kappa | \rho'_\kappa) \left( \frac{P_\kappa}{\rho_\kappa} \right) = (P'_\kappa P_\kappa + \rho'_\kappa \rho_\kappa), \qquad [9]$$
$$= (I_\kappa + \rho'_\kappa \rho_\kappa)$$

where $I_\kappa$ is a κ×κ identity matrix. By Bartlett's identity (1951), $$(I_\kappa + \rho'_\kappa \rho_\kappa)^{-1} = \left( I_\kappa - \frac{\rho'_\kappa \rho_\kappa}{1 + \rho_\kappa \rho'_\kappa} \right). \qquad [10]$$

Consequently, by noting that $$(P'_\kappa | \rho'_\kappa) \left( \frac{Y}{y} \right) = (P'_\kappa Y + \rho'_\kappa y), \qquad [11]$$

the estimate of θ from the (n+1)-observations augmented data is expressible as $$\hat{\theta}_{n+1} = \left( I_\kappa - \frac{\rho'_\kappa \rho_\kappa}{1 + \rho_\kappa \rho'_\kappa} \right) (P'_\kappa Y + \rho'_\kappa y) \qquad [12]$$
$$= \hat{\theta}_n + \frac{\rho'_\kappa (y - \rho_\kappa \hat{\theta}_n)}{1 + \rho_\kappa \rho'_\kappa}$$

Utilizing Equation [6], the predicted value of y from the non-augmented n-observation data is $$\hat{y}_n = \rho_\kappa \hat{\theta}_n \qquad [13]$$

where, by utilizing Equation [12], the predicted value of y from the augmented (n+1)-observation data is $$\hat{y}_{n+1} = \rho_\kappa \hat{\theta}_{n+1} \qquad [14]$$
$$= \frac{\rho_\kappa \hat{\theta}_n + (\rho_\kappa \rho'_\kappa) y}{1 + \rho_\kappa \rho'_\kappa}$$

with corresponding expectations based on the model given in Equation [6] of $$E(\hat{y}_n) = \rho_\kappa \theta, \qquad [15]$$

and $$E(\hat{y}_{n+1}) = \frac{\rho_\kappa \theta + (\rho_\kappa \rho'_\kappa) \mu_{n+1}}{1 + \rho_\kappa \rho'_\kappa}, \qquad [16]$$

where $\mu_{n+1} = E(y)$. Note here that the expected, or true value of the future observation is not necessarily equal to the expected value of its least-squares estimate based on the linear model given in Equation [6]. That is to say that the least-squares predictor based on the model [6] is baised with respect to the true value of the future observation. However, since $\hat{y}_n$ is the only accessible predictor, it is natural to assess the prediction error of y around the expected value of $\hat{y}_n$. On this basis, the mean squared error of prediction for y is $$MSEP(y) = E(y - \hat{y}_n)^2 \qquad [17]$$
$$= (1 + \rho_\kappa \rho'_\kappa) \sigma^2 + (\mu_{n+1} - \rho_\kappa \theta)^2$$

where $I_n \sigma^2 = E(ee')$ from Equation [6] and the definition of Y. An unbiased sample estimate of [17] is $$MSEP(\hat{y}_n) = (y - \rho_\kappa \hat{\theta})^2. \qquad [18]$$

In practice, one wishes to estimate the values, y, of a set of putative genotypes. From Equation [18] it is easy to see that the prediction equation should be characterized by a value of κ which minimizes the squared residuals of estimated values of future observations. An estimate of the mean squared error of prediction of future observations is, of course, impossible. Consequently, the prediction model is built solely on the non-augmented data. One proceeds by dropping each observation in turn from the data set and predicting the value of the dependent variable of the deleted observation via a model predicated upon the observations remaining in the data set. The mean squared error of prediction is then calculated as the average square of the difference between observed and predicted values of the dependent variable for all observations in the full data set.

Letting $q_\kappa$ represent a row vector deleted from $P_\kappa$, and z represent the value of the corresponding observation, the estimate of θ from the (n−1)-observations reduced data is $$\hat{\theta}_{n-1} = \hat{\theta}_n - \frac{q'_\kappa (z - q_\kappa \hat{\theta}_n)}{1 - q_\kappa q'_\kappa}, \qquad [19]$$

while the predicted value of z is $$\hat{z}_{n-1} = \frac{q_\kappa \hat{\theta}_n - (q_\kappa q'_\kappa) z}{1 - q_\kappa q'_\kappa} \quad [20]$$

with corresponding expected value $$E(z_{n-1}) = \frac{q_\kappa \theta - (q_\kappa q'_\kappa) \mu_{n-1}}{1 - q_\kappa q'_\kappa} \quad [21]$$

where $\mu_{n-1} = E(z)$.

Following the same line of reasoning leading to Equation [18], the expected mean squared error of prediction of the estimate of z from the (n−1)-observation reduced data is $$\begin{aligned} MSEP(z) &= E(z - \hat{z}_{n-1})^2 \quad [22] \\ &= \sigma^2 + \left( \frac{\mu_{n-1} - \rho_\kappa \theta}{1 - q_\kappa q'_\kappa} \right) \sigma^2 \end{aligned}$$

An unbiased sample estimate of [22] is provided by $$\widehat{MSEP}(z) = \frac{(z - \hat{z}_n)^2}{(1 - q_\kappa q'_\kappa)^2}. \quad [23]$$

The problem becomes simply that of determining the value of κ minimizing the weighted squared residuals of the predicted values. A methodology quite useful for doing so is generalized cross-validation. Specifically, the optimum value of κ is given by $$\kappa_0 = \min \left[ cssq(P_\kappa'Y)/(n-\kappa)^2 \right] \quad [24]$$

where evaluation is over $\kappa=1$ to $\rho$, $P_\kappa$ is the first κ columns of a ρ-column P matrix and cssq indicates the cumulative sum of squares of vector elements.

To further refine the methodology, the predictor data matrix, X, can first be transformed into the space of the marker variables of a target set of genotypes by the transformation $Z=XU$ where U is the matrix of eigenvectors (arranged in columns) of the target set. Relevant target sets can include a set of genotypic standards, or controls, or any related set of genotypes.

4. Applying Results

Results obtained from evaluating the phenotypic and genotypic databases and defining an association between a phenotypic trait and a genetic marker are applied to a second plant or plant line to predict the value of a particular numerically representable phenotypic trait in that plant. A process of the present invention, by predicting the value of a given phenotypic trait in a plant thus provides an improved means of selection in a plant breeding program. Detailed descriptions of the uses of a process of the present invention in enhancing the efficacy of selection in a plant breeding program are set forth hereinafter in Examples 1–3.

By way of example, selection can be applied to $F_x$ or $F_x(F_m)$ generation individuals, or $F_y(F_x(F_m))$ lines using tms values from Equation [3]. If large numeric values of the dependent variable, ($Y_i$ in Equation [2]) are favored, then large values of tms from Equation [3] are favored, and vice versa.

Several selection schemes are applicable:

a. Selection based on tms values of $F_x$ individuals, only.

b. Initial selection based on testcross performance of $F_n(F_m)$ lines followed by selection based on tms values of $F_x(F_m)$ individual, or $F_y(F_x(F_m))$ line, descendants of $F_m$ progenitors of selected $F_n(F_m)$ lines.

c. Selection via an index based on the simultaneous consideration of $F_n(F_m)$ line testcross performance and tms values of the corresponding $F_x(F_m)$ individual, or $F_y(F_x(F_m))$ line, descendants of the $F_m$ progenitors of the $F_n(F_m)$ lines.

Obviously, for $F_x$ individuals not descended from $F_m$ progenitors of $F_n(F_m)$ lines, only selection scheme (a) is possible. Theory applicable to selection schemes (b) and (c) has been presented by Cochran (1951). Schemes b and c are forms of 2-stage selection. They differ from all previously reported schemes in that selection criteria applied in the second stage are based on phenotypic observations the first stage of selection. In the previous schemes, repeated testcrosses were necessary. In the present invention, a testcross to evaluate the phenotype is needed only once and the information is transferred to the genotyped markers in advanced generations. The weights applied in the index used in selection scheme (c) can be obtained experimentally by means of calculation of the multiple regression of testcross yield of $F_x(F_m)$ individuals (or $F_y(F_x(F_m))$ lines) on tms scores of $F_x(F_m)$ individuals (or $F_y(F_x(F_m))$ lines) and testcross performance of $F_n(F_m)$ lines. Ostensibly the regression is estimated using a sample of the total $F_n(F_m)$ lines employed in the early generation testcross evaluation and a corresponding sample of testcrossed $F_x(F_m)$ individuals or $F_y(F_x(F_m))$ lines. The estimated regression coefficients are then used as weights in the index. Alternatively, the breeder can use any weights suggested by experience or judgement. It should be noted that the tester(s) utilized in the testcrosses of the $F_x(F_m)$ individuals or $F_y(F_x(F_m))$ lines need not be the same as that (those) employed in the testcrosses of the $F_n(F_m)$ lines.

The following Examples are illustrative of the present invention and are not limiting of the specification and claims in any way.

EXAMPLES

Example 1

Demonstration of the Efficacy of the Methods of This Invention for Corn Genotype Selection The efficacy of the methods of this invention was tested in two experiments, 2A and 2B, each conducted in two different years. For each experiment, a different $F_1$ hybrid (resulting from crosses between inbred lines designated (D188F×D196) and (K002×K592.-1)) had previously been produced and through self-pollination, a number of $F_3(F_2)$ and $F_5(F_2)$ lines were produced (FIG. 3). Each line was crossed to two testers as indicated. For 2A, the tester lines were designated K664A and K002. For experiment 2B, the testers were designated D196 and D759. For testcross evaluation, two $F_5(F_2)$ lines within each $F_3(F_2)$ line were included in the experiments. The sublining was executed at the $F_4$ generation; that is seed from ears of two different plants in each $F_4(F_2)$ line produced the two $F_5(F_2)$ sublines.

For experiment 2A, at each of the six locations in both years, the 288 testcrosses were evaluated in six 7×7 simple lattice blocks to reduce errors from for example, soil variability. In each block, testcrosses of 8 $F_3(F_2)$ and 16 corresponding descendant $F_5(F_2)$ lines to each of the two testers were grown. A filler entry (a standard commercial hybrid) rounded out the total of 49 entries per lattice block.

For experiment 2B, 384 testcrosses were evaluated in eight 7×7 simple lattice blocks at each of four locations in year 1. Because of seed shortages, only 288 testcrosses could be evaluated in experiment 2B in the second year. Of these, only 282 were common in both years (replicates). Only these 282 were included in the final data analysis. The testcrosses evaluated in the second year were arranged in six 7×7 simple lattice blocks and were grown, again, at four locations. In both years, the total of 49 entries in each 7×7 lattice was rounded out by a commercial check entry. The distribution of $F_3(F_2)$ and $F_5(F_2)$ testcrosses in each of the experiment 2B 7×7 lattice blocks was the same as that in the experiment 2A lattice blocks.

Two-row plots, 20 feet long, were used in both experiments. All plots were machine planted and harvested. Plots were overplanted and thinned back to stands equivalent to 21,000 plants per acre. Soil fertility levels, weed and insect pest controls, and general plot management were consistent with good agronomic practice.

Shelled grain weight from each plot was adjusted to 15.5% moisture, and the means of each entry were calculated using standard simple lattice inter and intrablock adjustment factors (see Cochran and Cox, 1957).

While the testcross trials were being evaluated during year 1, all lines involved were typed by restriction fragment length polymorphism (RFLP) analysis. The typing was accomplished by utilization of 78 single-copy probes for the lines in experiment 2A and 67 single-copy probes in experiment 2B Table 2; (see Weber and Helentjars, 1989). For both experiments 2A and 2B, the probe locus sites were known to be distributed fairly evenly across the genome by previous mapping. (Weber and Helentjaris, 1989).

The RFLP genotypes of each line at each probe locus was then given a numeric value as outlined in the methods. A separate regression equation was calculated for each year x tester combination at each probe locus in both experiments. In each regression, moisture-adjusted weight of shelled grain (yield) of each $F_3(F_2)$ line testcross averaged over locations in each year was the dependent variable. The independent variable in each regression was the numeric value of RFLP scores at the particular RFLP locus. The estimated regression coefficients were then used to produce total marker scores of each $F_5(F_2)$ line as described herein. All RFLP loci were included in the summation to produce the total marker score (tms) for each $F_5(F_2)$ line for each year x tester combination in each experiment.

Of paramount interest was prediction of performance across years. Also of interest was prediction across testers. Consequently, the regression of $F_5(F_2)$ testcross yield for each tester in each year on $F_3(F_2)$ testcross yield and $F_5(F_2)$ tms value for the same, and the opposite tester, in opposite years was calculated. Because in each experiment there were four (year x tester) combinations, eight separate regression equations were calculated in each experiment: four on the same tester, and four on the opposite tester in the opposite year.

TABLE 1

| Structure of Experiments 2A and 2B* | | |
|---|---|---|
| Attribute | Experiment 2A | Experiment 2B |
| $F_1$ Hybrid | D188F.D196 | K002.K592-1 |
| Testers | K664A,K002 | D196,D759E |
| No. $F_3(F_2)$ testcrosses per tester (year 1) | 48 | 47 |
| No. $F_5(F_2)$ testcrosses per tester (year 1) | 96 | 94 |
| No. $F_3(F_2)$ testcrosses per tester (year 2) | 48 | 47 |
| No. $F_5(F_2)$ testcrosses per tester (year 2) | 96 | 94 |

TABLE 1-continued

| Structure of Experiments 2A and 2B* | | |
|---|---|---|
| Attribute | Experiment 2A | Experiment 2B |
| No. locations (year 1)+ | 6 | 4 |
| No. locations (year 2)++ | 6 | 4 |

+For Experiment 2A: Waterman, IL; Remington, IN; Dayton, IA; Owatonna, MN; Spencer, IA; Pocahontas, IA.
For Experiment 2B: Gilman, IL; Streator, IL; Thomasboro, IL; and Grinnell, IA.
++For Experiment 2A: Waterman, IL; Remington, IN; Palm Grove, IA; Owatonna, MN; Spencer, IA; Pocahontas, IA.
For Experiment 2B: Gilman, IL; Streator, IL; Thomasboro, IL; and North Liberty, IA.
*Showing only the 282 testcross replicates.

TABLE 2

| Probes 2A | Probes 2B |
|---|---|
| 290 | 105 |
| 321 | 232 |
| 350 | 290 |
| 563 | 445 |
| B3-04 | B3-04 |
| 120 | 120 |
| 209B | 290B |
| 225 | 225 |
| 234 | 238 |
| 238 | 258 |
| 234 | 401 |
| 258 | 406 |
| 260B | 447 |
| 401 | B-725 |
| 406 | 239 |
| 428 | 242 |
| 447 | 297 |
| 566 | 298 |
| 589 | 402 |
| 608B | 456 |
| B7-25 | 591 |
| 123A | 607 |
| 239 | B845 |
| 242 | 108 |
| 297 | 212 |
| 403B | 296 |
| 405 | 425 |
| 591 | 386 |
| 268B | 396 |
| 296 | 444 |
| 388B | 451 |
| 425 | 465 |
| 446 | 594 |
| 457 | UMC19 |
| B123B | 115 |
| B15-2 | 256 |
| B8-15 | 282 |
| 208 | 409 |
| 396 | 449 |
| 451 | 101 |
| 594 | 235 |
| UMC19 | 265 |
| UMC31 | 280 |
| 256 | 393 |
| 282 | B629 |
| 288 | 113 |
| 409 | 123B |
| 449 | 385 |
| 223 | 391 |
| 235 | 394 |
| 280 | 433 |
| 373 | 596 |
| 419 | 611 |
| 608A | 110 |
| B5-47 | 114 |
| B6-29 | 218 |
| 113 | 426 |

TABLE 2-continued

| Probes 2A | Probes 2B |
|---|---|
| 123B | 558 |
| 263 | B123 |
| 394 | UMC48 |
| 433 | 211 |
| 596 | 253 |
| B16-06 | 266 |
| 107 | 293 |
| 110 | 403 |
| 114 | 427 |
| 220 | UMC95 |
| 426 | |
| 438 | |
| B123A | |
| UMC48 | |
| 211 | |
| 253 | |
| 266 | |
| 403 | |
| B14-28 | |
| BRZ-1 | |
| WAXY | |

(Weber and Helentjaris, 1989)

Though heterogeneity among individual regressions was evident in both experiments, in each instance $F_5(F_2)$ tms value accounted for as much or more variation in $F_5(F_2)$ testcross yield as did $F_3(F_2)$ testcross yield itself. The corrected sums of squares and cross products from the individual regressions were pooled to produce summary regression analyses for the same and opposite testers in opposite years in each experiment (Tables 3 and 4). The analyses of variance results for both experiments indicate that, not only will prediction from tms values enhance prediction from $F_3(F_2)$ testcross yield, but that $F_5(F_2)$ tms value is a superior predictor compared to $F_3(F_2)$ testcross yield. Hence, the method appears to be effective.

TABLE 3

Pooled Regression Analysis of $F_5(F_2)$ Testcross
Yield on $F_3(F_2)$ Testcross Yield and $F_5(F_2)$ tms Value
From the Opposite Year. Experiment 2A.

| | | Mean Square† | |
|---|---|---|---|
| Source | df | Tester 1 | Tester 2 |
| $F_3(F_2)$ testcross yield and $F_5(F_2)$ tms value | 8 | 403** | 259** |
| $F_3(F_2)$ testcross yield | 4 | 397** | 227** |
| $F_5(F_2)$ tms value | 4 | 758** | 501** |
| $F_5(F_2)$ rflp score after $F_3(F_2)$ testcross yield | 4 | 408** | 292** |
| Residual | 352 | 42 | 45 |

**indicates significance of the F test at the 0.01 level.
†tester 1 is the tester for the $F_3(F_2)$ generation lines that is identical to the tester for the $F_5(F_2)$ generation lines; tester 2 is the opposite tester and is not the same tester for the $F_3(F_2)$ lines as was used to evaluate the $F_5(F_2)$ lines.

TABLE 4

Pooled Regression Analysis of $F_5(F_2)$ Testcross
Yield on $F_3(F_2)$ Testcross Yield and $F_5(F_2)$ tms Value
From the Opposite Year. Experiment 2B.

| | | Mean Square† | |
|---|---|---|---|
| Source | df | Tester 1 | Tester 2 |
| $F_3(F_2)$ testcross yield and $F_5(F_2)$ tms value | 8 | 255** | 309** |
| $F_3(F_2)$ testcross yield | 4 | 334** | 417** |
| $F_5(F_2)$ tms value | 4 | 477** | 570** |
| $F_5(F_2)$ rflp score after $F_3(F_2)$ testcross yield | 4 | 176** | 200** |
| Residual | 340 | 37 | 36 |

**indicates significance of the F test at the 0.01 level.
†tester 1 is the tester for the $F_3(F_2)$ generation lines that is identical to the tester for the $F_5(F_2)$ generation lines; tester 2 is the opposite tester and is not the same tester for the $F_3(F_2)$ lines as was used to evaluate the $F_5(F_2)$ lines.

Example 2

A Process of Improving the Efficacy of A Soybean Breeding Program

Soybeans are unusual among the oilseed crops in that their protein content is high, marketable and worthy of improvement. The soybean contains about twice as much protein as oil (41 percent versus 21 percent) and the total market value of the protein usually approaches that of the oil. Protein and oil contents are negatively correlated, so the breeder must set minimum standards for one while selecting for the other. Higher protein levels have been achieved with protein, oil and yield when the traits were assigned equal economic weights in a selection index. Selection for either oil or protein increases the seed content of that component but greatly reduces yield. Only when the selection index includes yield does this trail increase. Improvements of total oil and protein yield can best be achieved by selecting for yield, while maintaining or slightly increasing oil and protein percentages. For general information on vegetative and reproductive stages in soybeans, see Fehr and Caviness, 1977.

This example presents methods liar predicting advanced inbred generation soybean line performance from early generation line performance, using genetic markers. An example of genetic markers in soybeans are RFLP's (Keim, et al., 1990). Methods of detecting RFLP markers in soybeans are also presented by Keim.

The method is as follows:

1. Produce a seminal $F_1$ hybrid by crossing two essentially homozygous cultivars, e.g., *Glycine max* (publically available variety Williams) and *Glycine soja* (from the wild, ATCC Accession No. PI 81762). Lines are grown in plots, for example 1.5 meters long at 33 seeds per meter separated by 1.2 meters within rows with 1 meter spacing between rows.

2. Via natural self-pollination, produce a number of $F_n$ generation lines within $F_m$ generation individuals ($F_n(F_m)$); m=2, ..., ; n=m, m+1, m+2, ..., .

3. Evaluate the $F_n(F_m)$ lines to determine yield and percentage of oil and protein in standard field trials at one or more locations for one or more years. These trials control for variation in soil composition, inherent soil nutrients, mineral content, and other environmental factors (Cochran and Cox, 1957).

4. Score the $F_n(F_m)$ lines for the presence or absence of the parental alleles of each genetic marker[1] (RFLP, isozymes, polymorphic amplified DNA).

[1] Soybeans are less polymorphic than corn; consequently, interspecific crosses are preferred.

5. Convert the marker scores to a numeric scale consistent with the phenotypic expression of the markers.

6. Estimate the functional relationships between the markers and the phenotypic expression of a linear combination of yield and percent oil and protein by means of a regression equation of the form:

$$Y_i = \mu + \sum_{k=1}^{t_j} B_{jk}X_{ijk} + \epsilon_i$$

where $Y_i$=phenotypic expression of the linear combination of traits of interest of the $i^{th}F_n(F_m)$ line (i=1, 2, ..., l);

$\mu$=mean phenotypic expression of all $F_n(F_m)$ lines evaluated;

$B_{jk}$=coefficient of the regression of Y on the $k^{th}$ marker locus in the $j^{th}$ combination of markers (j=1, 2, ..., s; k=1, 2, ..., $t_j$);

$X_{ijk}$=numeric value of the $k^{th}$ marker in the $j^{th}$ combination of markers for the $i^{th}$ $F_n(F_m)$ line;

$\epsilon_i$=deviation from regression for the $i^{th}$ $F_n(F_m)$ line.

7. Derive by natural self-pollination, a number of $F_x$ or $F_x(F_m)$ (x≧n) individuals, or $F_y(F_x(F_m))$ (y>x) lines, from the seminal $F_1$ hybrid.

8. Score the marker types of the $F_x$ or $F_x(F_m)$ individuals, or $F_y(F_x(F_m))$ lines, in a manner consistent with the scoring of the $F_n(F_m)$ lines and, likewise, convert the scores to a numeric scale.

9. Calculate a total marker score (tms) for each $F_x$ or $F_x(F_m)$ individual, or $F_y(F_x(F_m))$ lines, as follows:

$$tms_v = \sum_{u=1}^{g} \hat{B}_u Z_{uv}, (g \leq \Sigma t_j),$$

where $tms_v$=total marker score of the $v^{th}$ $F_x$ or $F_x(F_m)$ individual, or $F_y(F_x(F_m))$ line, (v=1, 2, ..., h);

$\hat{B}_u$=regression coefficient estimate for the $u^{th}$ marker locus;

$Z_{uv}$=numeric value of the $u^{th}$ marker for the $v^{th}$ $F_x$ or $F_x(F_m)$ individual, or $F_y(F_x(F_m))$ line.

10. Apply selection to the $F_x$ or $F_x(F_m)$ individuals or $F_y(F_x(F_m))$ lines by:

a. selection based on tms values only;

b. initial selection based on performance of $F_n(F_m)$ line performance of $F_m$ progenitors followed by selection based on tms values of $F_x(F_m)$ individual, or $F_y(F_x(F_m))$ line descendants of progenitors of selected $F_n(F_m)$ lines; and c. selection based on simultaneous consideration of $F_n(F_m)$ line performance and tms values of $F_x(F_m)$ individual, or $F_y(F_x(F_m))$ line descendants of $F_m$ progenitors.

(For soybeans, yields of 45–50 bushels per acre are considered to be satisfactory.)

Example 4

Plants of Different Lineage

To test a process of this invention on plants of differing lineage, parental genotypes from 722 F1 hybrids evaluated for yield in 1990 DeKalb Plant Genetics advanced performance trials were RFLP typed using 60 single copy probe/enzyme combinations (See Table 5 below).

Though generalized cross-validation has produced optimum results in our experience, similar prediction methodologies can be employed (Hocking, 1976; Martens and Naes, 1987) featuring predictor variables in a regression model based on the correlation of an observed phenotype with the genetic markers in a general population of predictor genotypes.

TABLE 5

| CHROMOSOME | PROBE | ENZYME |
|---|---|---|
| 1 | 120 | SST |
| 1 | 234 | HINDIII |
| 1 | 236 | HINDIII |
| 1 | 238 | HINDIII |
| 1 | 401 | ECORI |
| 1 | 406 | HINDIII |
| 1 | 447 | HINDIII |
| 1 | B725 | ECORI |
| 2 | 239 | HINDIII |
| 2 | 297 | HINDIII |
| 2 | 298 | ECORI |
| 2 | 402 | HINDIII |
| 3 | 212 | SST |
| 3 | 247 | ECORI |
| 3 | 257 | SST |
| 3 | 296 | HINDIII |
| 3 | 432 | HINDIII |
| 3 | 446 | SST |
| 3 | 457 | ECORI |
| 3 | B815 | HINDIII |
| 4 | 386 | HINDIII |
| 4 | 396 | ECORI |
| 4 | 444 | HINDII |
| 4 | 451 | HINDIII |
| 4 | UMC19 | HINDIII |
| 4 | UMC31 | ECORI |
| 4 | UMC31 | SST |
| 5 | 213 | SST |
| 5 | 288 | SST |
| 5 | 295 | ECORI |
| 5 | 408 | HINDIII |
| 5 | 409 | HINDIII |
| 5 | 579 | ECORI |
| 6 | 223 | ECORI |
| 6 | 252 | HINDIII |
| 6 | 280 | HINDIII |
| 6 | 373 | ECORI |
| 7 | 263 | ECORI |
| 7 | 391 | HINDIII |
| 7 | 392 | SST |
| 7 | 455 | HINDIII |
| 8 | B107 | SST |
| 8 | 110 | SST |
| 8 | 114 | ECORI |
| 8 | 268 | HINDIII |
| 8 | 438 | ECORI |
| 8 | 585 | HINDIII |
| 8 | B2369 | SST |
| 8 | UMC48 | ECORI |
| 9 | 209 | ECORI |
| 9 | 211 | ECORI |

TABLE 5-continued

| CHROMOSOME | PROBE | ENZYME |
| --- | --- | --- |
| 9 | 266 | SST |
| 9 | B713 | SST |
| 9 | B2 | ECORI |
| 9 | UMC95 | SST |
| 9 | WAXY | ECORI |
| 10 | 264 | HINDIII |
| 10 | 306 | HINDIII |
| 10 | 445 | ECORI |
| 10 | 304 | ECORI |

Ten predictor data sets, each with a corresponding data set of genotypes to be predicted, were derived by random sampling the entire set of 722 with replacement. The sampling was conducted so as to produce predictor data sets with approximately 600 observations with the remaining observations consigned to the data set for prediction.

The g vectors for the observations in each data set were constructed using a value of h=0.5, thus putting equal emphasis on heterozygotes and homozygotes. The predictor data sets were then transformed by the matrix of eigenvectors of the corresponding data set targeted for prediction, and a prediction model for each transformed predictor data set was derived by generalized cross-validation. For each predicted data set predicted and observed, yields were correlated with the following results (Table 6).

TABLE 6

Correlations Between Predicted And Actual Yields In Randomly Sampled Sets Of Hybrids Evaluated For Yield In 1990 Performance Trials.

| No. of Observations | | |
| --- | --- | --- |
| Predictor Data | Predicted Data | Correlation Between Observed and Predicted Yield |
| 629 | 93 | 0.31** |
| 618 | 104 | 0.29** |
| 603 | 119 | 0.37** |
| 624 | 98 | 0.32** |
| 610 | 112 | 0.32** |
| 625 | 97 | 0.37** |
| 624 | 98 | 0.48** |
| 620 | 102 | 0.35** |
| 611 | 111 | 0.20* |
| 623 | 99 | 0.38** |

*, **indicate significance at the 0.05 and 0.01 levels, respectively.

The data show that a process of the present invention can be used to predict the occurrence of a phenotypic trait in a second plant using an association between genotype and phenotype in a first plant, where the first and second plants are derived from different seminal $F_1$ hybrids.

While the invention is susceptible to various modifications and alternative forms, specific embodiments thereof have been shown by way of example in the drawings and are herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below and all references cited in the specification are incorporated herein by reference to the extent that they supplement, explain, provide a background for, or teach methodology, techniques, and/or compositions employed herein.

Allen, D. M. (1971) "Mean Square Error of Prediction as a Criterion for Selecting Variables," *Technometrics* 13:469–475

Allen, D. M. (1974) "The Relationship Between Variable Selections and Data Augmentation and a Method for Prediction," *Technometrics* 16: 125–127.

Asins, M. J. (1988) "Detection of Linkage Between Restriction Fragment Length Polymorphism Markers and Quantitative Traits," *Theor. App. Genet.* 76:623–626.

Axtell, J. D. (1981) "Breeding for improved Nutritional Quality," Chap. 10, In *Plant Breeding II*, K. J. Frey, ed., Iowa State Univ. Press.

Bartlett, M. S. (1951) "An Inverse Matrix Adjustment Arising in Discriminant Analysis," *Ann. Math. Statist.* 22:107.

Beckmann, J. S. and Soller, M. (1983) "Restriction Fragment Length Polymorphisms in Genetic Improvement: Methodologies, Mapping and Costs," *Theor. Appl. Genet.* 67:35–43.

Botstein, D., White, R., Skolnick, M., et al. (1980) "Construction of a Genetic Linkage Map in Man Using Restriction Fragment Length Polymorphisms," *Am. J. Hum. Genet.* 32:314–331.

Burr, B., Evola, E., Burr, F., et al. (1983) "The Application of Restriction Fragment Length Polymorphisms to Plant Breeding," Settoco, J.K. and Hollaender, A. (eds.) *Genetic Engineering Principles and Methods*, Plenum Press, New York and London, pp. 45–59.

Caldwell, B. E., Weber, C. R. and Byth, D. E. (1966) "Selection Value of Phenotypic Attributes in Soybeans," *Crop Sci.* 6:249–251.

Cochran, W. G. (1951) "Improvement by selection." Proc. 2nd Berkeley Symp. Math. Stat. and Prob. pp. 449–470.

Cochran, W.G. and Cox, G. M. (1957) *Experimental Designs*, 2nd Ed. John Wiley & Sons, New York.

Draper, N. R. and Smith, H. (1968) *Applied Regression Analysis*, John Wiley & Sons, New York.

East, E. M. (1916) "Studies on Size Inheritance in Nicotiana." *Genetics* 1: 164–176.

East, E. M., Jones, D. F. (1919) *Inbreeding and Outbreeding*, J. B. Lippincott Co., Phil.

Evola, S. V., Burr, J. A., and Burr, B. (1986) "The Suitability of Restriction Fragment Length Polymorphisms as Genetic Markers in Maize." *Theor. App. Genet.* 71:765–771.

Falconer, D. S. (1960) "Introduction to Quantitative Genetics," Ronald Press Co., New York.

Fehr, W. R. and Caviness, C. E. (1977) "Stages of Soybean Development," Iowa Agric. Home Economics Exp. Stn., Iowa Coop. Ext. Serv. Spec. Rep. 80.

Fisher, R. A. (1918) "Correlation Between Relatives on the Supposition of Mendalian Inheritance." *Trans. Royal Soc. Edinburgh.* 52:399–433.

Hallauer, A. R. and Miranda, J. B. (1981) *Quantitative Genetics in Maize Breeding*, Chap. 8, Iowa State University Press, Ames.

Hallauer, et al. (1988) "Corn Breeding-Testers and Testing," In: *Corn and Corn Improvement*, Sprague, G. F. and Dudley, J. W., eds., pp. 463–564.

Helentjaris, T., King, G., Slocum, M., et al. (1985) "Restriction Fragment Polymorphisms as Probes for Plant Diversity and Their Developments as Tools for Applied Plant Breeding," *Plant Mol. Biol.* 5:109–118.

Helentjaris, T., Slocum, M. Wright, S., et al., (1986) "Construction of Genetic Linkage Maps in Plants Using Restriction Fragment Polymorphisms," *Theor. Appl. Genet.* 72:761–769.

Hocking, R. R. (1976) "The Analysis and Selection of Variables in Linear Regression," *Biometrics* 32: 1–49.

Golub, G. H., Heath, M., and Wahba, G. (1979) "Generalized Cross-Validation as a Method for Choosing a Good Ridge Parameter," *Technometrics* 21:215–223.

Innis, et al. (eds.) *PCR Protocols*, Academic Press, New York (1990).

Johannsen, W. (1909) "Elements der Evokten Erbelichkeirsllehre, Fishcher, Jena."

Keim, P., Diers, B. W., Olson, T. C., et al. (1990) "RFLP Mapping in Soybean: Assocation Between Marker Loci and Variation in Quantitative Traits," *Genetics* 126:735–742.

Lande, R. and Thompson, R. (1990) "Efficiency of Marker-Associated Selection in the Improvement of Quantitative Traits," *Genetics* 124:743–756.

Lander, E. S. and Botstein, D. (1989) "Mapping Mendelian Factors Underlying Quantitative Traits Using RFLP Linkage Maps," *Genetics* 121:185–199, see also WO 90104651.

Lee, D. Ellis, F. H. N., Turner, R. P. et al. (1990) "A Copia-like Element in Pisum Demonstrates the Uses of Dispersed Repeated Sequences in Genetic Analysis." *Plant Molecular Biology* 15:707–720.

Martens, H., and Naes, T. (1987) "Multivariate Calibration by Data Compression. Near-Infrared Technology in the Agricultural and Food Industries. Eds. Williams, P. and Norris, K., St. Paul, Minn.: *American Assn. of Cereal Chemists*.

Mather, K. and Jinks, J. L. (1971) *Biometrical Genetics*, Cornell Univ. Press, Ithaca, N.Y.

Nienhuis, J., Helentjaris, T., Slocum, M. (1987) "Restriction Fragment Length Polymorphism Analysis of Loci Associated with Insect Resistance in Tomato," *Crop Sci.* 27:797–803.

Nilsson-Ehle, H. (1909) "Kreuzungunter-schungen an Hafer und Weizen Lund."

Paterson, A. H., et al. (1988) "Resolution of Quantitative Traits into Mendelian Factors by Using a Complete Linkage Map of Restriction Fragment Polymorphism," *Nature* 335:721–724.

Smith, C. (1967) "improvement of Metric Traits Through Specific Genetic Loci," *Anim. Pract.* 9:349–358.

Sprague, G. F. and Eberhart, S. A. (1977) "Corn Breeding," in *Corn and Corn Improvements*, J. A. Dudley and G. F. Sprague (eds), Iowa State Univ. Press.

Stuber, C. W., Goodman, M. M. and Moll, R. H. (1982) "Improvement in Yield and Bar Number Resulting from Selection at Allozyme Loci in a Maize Population," *Crop Sci.* 22:737–740.

Tanskley, J. A., Sprague, G. F. and Orton, *Isozymes in Plant Genetics and Breeding* 1B (Elsevier, N.Y., 1983).

Wahba, G. and Wold, S. (1975) "A Completely Automatic French Curve: Fitting Spline Functions by Cross-Validation," *Comm. in Statist.* 4:1–17.

Williams, J. G. K. et al. (1990) "DNA Polymorphisms Amplified by Arbitrary Primers are Useful as Genetic Markers," *Nucleic Acids Research* 18:6531–6535.

Weber, D. and Helentjaris, T. (1989) "Mapping RFLP Loci in Maize Using B-A Translocations," *Genetics* 121:583–590.

Wright, S., *Evolution and the Genetics of Populations*, vol. 1 (1968), vol. 5 (1977), Univ. of Chicago Press, Chicago.

EP 0 306 139 A2, "Identification, Localization and Introgression into Plants of Desired Multigenic Traits."

PCT/US 89/00709, "Genetic Linkages Between Agronomically Important Genes and Restriction Fragment Length Polymorphisms."

What is claimed is:

1. A process for predicting the phenotypic trait of yield in a plant of a progeny maize population through analysis of genotypes of a first and second single cross hybrid maize population, said process comprising the steps of:

(a) quantitatively assessing the distribution of said phenotypic trait of yield in members of said first plant population;

(b) genotyping members of both populations for an inherited genetic marker;

(c) evaluating said phenotypic trait in conjunction with the genotype of said first plant population to define an association between said phenotypic trait and said inherited genetic marker;

(d) predicting the value of the phenotypic trait of yield in progeny of said second plant population using said association, and (e) selecting progeny of said second population based on said association.

2. The process according to claim 1 wherein said association is a regression equation in which said phenotypic trait of yield is a dependent variable and said inherited genetic marker is an independent variable.

3. The process according to claim 1 wherein said first and said second plant populations are both derived from the same seminal $F_1$ hybrid, said second plant population being at the same or an advanced generation as said first plant population.

4. The process according to claim 1 wherein quantitatively assessing comprises testcrossing to obtain progeny and quantitatively assessing the distribution of combining ability of said members of first plant population.

5. The process according to claim 1 wherein quantitatively assessing comprises making direct observations on progeny derived by artificial or natural self-pollination of said first plant population.

6. The process according to claim 1 wherein said inherited genetic marker is inherited in codominant fashion.

7. The process according to claim 1 wherein said inherited genetics marker is inherited in dominant fashion.

* * * * *

UNITED STATES PATENT AND TRADEMARK OFFICE
CERTIFICATE OF CORRECTION

PATENT NO. : 5,492,547
DATED : February 20, 1996
INVENTOR(S) : Richard Johnson

It is certified that error appears in the above-indentified patent and that said Letters Patent is hereby corrected as shown below:

Title page, item [22], after Filed: Sep. 14, 1993" and before "Int. Cl.", insert-- Related U.S. Application Data Continuation-in-Part of Ser. No. 07/656,730, Feb. 19, 1991, abandoned--.

Column 30, line 6, delete "4" and substitute therefore --3--.

Signed and Sealed this

Eighth Day of April, 1997

Attest:

BRUCE LEHMAN

Attesting Officer

Commissioner of Patents and Trademarks

US005492547B1

REEXAMINATION CERTIFICATE (3563rd)

United States Patent [19]

Johnson

[11] B1 5,492,547

[45] Certificate Issued Jun. 30, 1998

[54] PROCESS FOR PREDICTING THE PHENOTYPIC TRAIT OF YIELD IN MAIZE

[75] Inventor: Richard Johnson, Urbana, Ill.

[73] Assignee: DeKalb Genetics Corp., DeKalb, Ill.

Reexamination Request:
No. 90/004,474, Nov. 8, 1996

Reexamination Certificate for:
Patent No.: 5,492,547
Issued: Feb. 20, 1996
Appl. No.: 121,391
Filed: Sep. 14, 1993

Certificate of Correction issued Mar. 12, 1997.

Related U.S. Application Data

[63] Continuation-in-part of Ser. No. 656,730, Feb. 19, 1991, abandoned.
[51] Int. Cl.$^6$ .............................. A01H 1/00; C12N 15/00
[52] U.S. Cl. .................. 47/58; 435/172.3; 800/DIG. 56
[58] Field of Search ........................... 47/58, DIG. 1; 435/172.3, 172.1; 800/200, 205, DIG. 56

[56] References Cited

U.S. PATENT DOCUMENTS

| 4,626,610 | 12/1986 | Sun ........................................ 800/1 |
| 4,670,388 | 6/1987 | Rubin et al. ...................... 435/172.3 |
| 5,385,835 | 1/1995 | Helentjaris et al. .. |

FOREIGN PATENT DOCUMENTS

| 0306139 | 1/1988 | European Pat. Off. ............ 435/172.3 |
| 0317239 | 12/1988 | European Pat. Off. ............ 435/172.3 |
| 84/04758 | 3/1984 | WIPO ............................. 435/172.3 |
| 89/07647 | 6/1989 | WIPO ............................. 435/172.3 |
| 90/04651 | 5/1990 | WIPO ............................. 435/172.3 |

OTHER PUBLICATIONS

Johnson, "RFLP-assisted Early Generation for Advanced Generation Testcross Performance," distributed at the 27th Annual Illinois Corn Breeder's School on Mar. 4–5, 1991.
Staff, "DeKalb Patents Gene That Predicts Yield," *Seed & Crops Industry 47*: 38 (May 1996).
Lande & Thompson, "Efficiency of Marker–Assisted Selection in the Improvement of Quantitative Traits," Genetics, 124:743–756, 1990.
Keim et al., "RFLP Mapping in Soybean: Association Between Marker Loci and Variation in Quantitative Traits," Genetics, 126:735–742, 1990.
Michelmore & Shaw, "Character Dissection," Nature, News and Views, 335:672–673, 1988.
Paterson et al., "Resolution of quantitative traits into Mendelian factors by using a complete linkage map of restriction fragment length polymorphisms," Nature, 335:721–726, 1988.
Nienhuis et al., "Restriction Fragment Length Polymorphism Analysis of Loci Associated with Insect Resistance in Tomato," Crop Sci., 27:797–803, 1987.
Lander & Botstein, "Mapping Mendelian Factors Underlying Quantitative Traits Using RFLP Linkage Maps," Genetics, 121:185–199, 1989.

Tanksley et al., Bio/Technology, 7:257–264, 1989.
Asins & Carbonell, Theor. Appl. Genet., 76:623–626, 1988.
Weller et al., Biol. Abstr., 85(9), Abstract #90101, 1988.
Helentjaris, Trends in Genetics, 3(8):217–221, 1987.
Osborn et al., Theor. Appl. Genet., 73:350–356, 1987.
Helentjaris & Shattuck–Eidens, Maize Genetics Corp. Newsletter, pp. 88–89, 1987.
Weller, Biol. Abstr., 85(6), Abstract #57768, 1988.
Weller, Biol. Abst., 83, Abstract #3756, 1987.
Lander et al., Genomics, 1(2):174–181, 1987.
Helentjaris, J. Cell. Biochem. Suppl. 11(3):56, Abstract #F429, 1987.
Helentjaris, Am. J. Botany, 74(5):665, Abstract #197, 1987.
Beckman & Soller, Oxford Surveys of Plant Molecular and Cellular Biology, 3:196–250, 1986.
Helentjaris et al., Theor. Appl. Genet., 72:761–769, 1986.
Evola et al., Theor. Appl. Genet., 71:765–771, 1986.
Bernatzky & Tanksley, Genetics, 112:887–898, 1986.
Smith & Simpson, Biol. Abstr. 82(12), Abstract #108250.
Soller & Beckman, Biol. Abstr. 82, Abstract #86937.
Helentjaris et al., Plant Mol. Biol., 5:109–118, 1985.
Soller & Beckman, Theor. Appl. Genet., 67:25–33, 1983.
Tanksley et al., Biol. Abstr. 76(6):4509, Abstract #41484.
Tanksley et al., Biol. Abstr. 73(10):7132, Abstract #68480.
Cox, "The FLP protein of the yeast 2–μm plasmid: Expression of a eukaryotic genetic recombination system in *Escherichia coli*", Proc. Natl. Acad. Sci. USA, 80:4223–4227, 1983.
Edwards, et al., "Molecular–Marker–Facilitated Investigations of Quantitative–Trait Loci in Maize. I. Numbers, Genomic Distribution and Types of Gene Action", Genetics, 116:113–125, 1987.
Jensen, "Selection Indices", In *Plant Breeding Methodology*, Wiley Interscience, 25:355–378, 1981.
Larsen and Hanway, "Corn Production", Chapter 11, 625–669.
Ou–Lee et al., "Expression of a foreign gene linked to either a plant–virus or a Drosophila promoter, after electroporation of protoplasts of rice, wheat and sorghum", Proc. Natl. Acad. Sci. USA, 83:6815–6819, 1986.
Poehlman, "Progeny Test Versus Combining Ability Test", Breeding Field Crops, Third Edition, p. 216.

*Primary Examiner*—Gary Benzion

[57] ABSTRACT

This invention relates to a method for improving the efficacy of a plant breeding program which has as its goal to selectively alter phenotypic traits that are capable of being described numerically and are under the control of quantitative trait loci (QTLs). The method combines the newer techniques of molecular biology with modifications of classical pedigree breeding strategies. Progeny performance is predicted on the basis of at least one secondary trait, facilitating selection strategies. In particular, regression estimates are obtained by determining the relationship between selected inherited marker loci and quantitative phenotypic trait values in predictor populations, and used in combination with inherited marker profiles of plants, to implement a selection strategy in related populations.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–7 is confirmed.

* * * * *